US007807135B2

(12) United States Patent
Kung et al.

(10) Patent No.: US 7,807,135 B2
(45) Date of Patent: *Oct. 5, 2010

(54) STILBENE DERIVATIVES AND THEIR USE FOR BINDING AND IMAGING AMYLOID PLAQUES

(75) Inventors: Hank F. Kung, Wynnewood, PA (US); Mei-Ping Kung, Wynnewood, PA (US); Zhi-Ping Zhuang, Lansdale, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1185 days.

This patent is subject to a terminal disclaimer.

(21) Appl. No.: 11/305,333

(22) Filed: Dec. 19, 2005

(65) Prior Publication Data

US 2006/0269473 A1 Nov. 30, 2006

Related U.S. Application Data

(60) Provisional application No. 60/636,696, filed on Dec. 17, 2004, provisional application No. 60/686,395, filed on Jun. 2, 2005.

(51) Int. Cl.
*A61K 51/00* (2006.01)
*A61M 36/14* (2006.01)

(52) U.S. Cl. ............... 424/1.89; 424/1.11; 424/1.65; 424/1.81; 424/1.85; 424/9.1

(58) Field of Classification Search ............... 424/1.11, 424/1.65, 1.81, 1.85, 1.89, 9.1, 9.2, 9.3, 9.4, 424/9.5, 9.6, 9.7, 9.8; 564/1, 305, 442
See application file for complete search history.

(56) References Cited

U.S. PATENT DOCUMENTS

| | | | |
|---|---|---|---|
| 5,521,213 | A | 5/1996 | Prasit et al. |
| 5,525,632 | A | 6/1996 | Obsumi et al. |
| 5,601,801 | A | 2/1997 | Flanagan et al. |
| 2003/0149250 | A1 | 8/2003 | Kung et al. |
| 2006/0002853 | A1 | 1/2006 | Kung et al. |
| 2006/0269474 | A1 | 11/2006 | Kung et al. |

FOREIGN PATENT DOCUMENTS

| | | |
|---|---|---|
| DE | 231432 A1 | 12/1985 |
| JP | 60247244 A | 12/1985 |

OTHER PUBLICATIONS

International Search Report for International Application No. PCT/US05/45682, United States Patent and Trademark Office, Alexandria, VA, mailed on Jun. 1, 2006.
International Search Report for International Application No. PCT/US05/45683, United States Patent and Trademark Office, Alexandria, VA, mailed on Dec. 12, 2006.
Ager, I.R., and Phillips, L., "$^{19}$F Nuclear Magnetic Resonance Studies of Aromatic Compounds. Part I. The Effect of Solvents on the Chemical Shift of Fluorine Nuclei in *para*-Substituted Fluorobenzenes, 4-Substituted 4'-Fluoro-*trans*-stilbenes, and 4-Substituted 3'-Fluoro-*trans*-stilbenes," *J. Chem. Soc., Perkin Trans. II*:1975-1982, 1993, The Chemical Society (1972).
Annunziata, R. And Colonna, S., "Stereochemistry of α-Halogenosulphoxides. Part 5. Absolute Stereochemistry of α-Chlorination of Benzyl t-Butyl Sulphoxide," *J. Chem. Soc., Perkin Trans. I*:1052-1056, The Chemical Society (1977).
Arbez-Gindre, C., et al., "Organolithium reagents bearing nonlinear optical chromophores. Synthesis of triarylmethane dyes," *Tetrahedron Lett.* 40:7413-7416, Elsevier Science Ltd. (1999).
Ashburn, T.T., et al., "Amyloid probes based on Congo Red distinguish between fibrils comprising different peptides," *Chem. Biol.* 3:351-358, Current Biology Ltd. (1996).
Attinà, M., et al., "Labeled Aryl Fluorides from the Nucleophilic Displacement of Activated Nitro Groups by $^{18}$F-F," *J. Labelled Comp. Radiopharm. XX.* 501-514, John Wiley & Sons, Ltd. (1983).
Berge, S.M. et al., "Pharmaceutical Salts," *J. Pharm. Sci.* 66:1-19, American Pharmaceutical Association (1977).
Counsell, R.E., et al.,"Radioiodinated Estrogens and Antiestrogens as Potential Imaging Agents," *Curr. Top. Mol. Endocrinol.* 4:107-113, Plenum Press (1976).
Diana, G.D., et al., "Antiviral Activity of Some β-Diketones. 4. Benzyl Diketones. In Vitro Activity against Both RNA and DNA Viruses," *J. Med. Chem.* 21:889-894, American Chemical Society (1978).
Elhaddaoui, A., et al., "Competition of Congo Red and Thioflavin S Binding to Amyloid Sites in Alzheimer's Diseased Tissue," *Biospectroscopy* 1:351-356, John Wiley & Sons Inc. (1995).
Findeis, M.A., "Approaches to discovery and characterization of inhibitors of amyloid β-peptide polymerization," *Biochim. Biophys. Acta* 1502:76-84, Elsevier Science B.V. (2000).
Gascoyne, J.M., et al., "Fluorine-19 Nuclear Magnetic Resonance Studies of Aromatic Compounds. Part 5. Transmission of Substituent Effects across Two Aromatic Rings connected by C—C and -C-Linkages," *J. Chem. Soc. Perkin Trans. II*:1051-1057, The Chemical Society (1977).
Ginsberg, S.D., et al., "Molecular Pathology of Alzheimer's Disease and Related Disorders," in *Cerebral Cortex*, Peters, A. and Morrison, J.H., eds., Kluwer Academic/Plenum Publishers, New York, NY, pp. 603-654 (1999).
Golde, T.E., et al., "Biochemical detection of Aβ isoforms: implications for pathogenesis, diagnosis, and treatment of Alzheimer's disease," *Biochim. Biophys. Acta* 1502:172-187, Elsevier Science B.V. (2000).
Han, H., et al., "Technetium Complexes for the Quantitation of Brain Amyloid," *J. Am. Chem. Soc.* 118:4506-4507, American Chemical Society (1996).
Ho, T.-I., et al., "Novel Photochemical Rearrangement of Styrylfurans," *Angew. Chem. Int. Ed. Engl.* 38:2558-2560, Wiley-VCH Verlag GmbH (1999).

(Continued)

*Primary Examiner*—D L Jones
(74) *Attorney, Agent, or Firm*—Woodcock Washburn LLP

(57) ABSTRACT

This invention relates to a method of imaging amyloid deposits and to labeled compounds, and methods of making labeled compounds useful in imaging amyloid deposits. This invention also relates to compounds, and methods of making compounds for inhibiting the aggregation of amyloid proteins to form amyloid deposits, and a method of delivering a therapeutic agent to amyloid deposits.

35 Claims, 1 Drawing Sheet

OTHER PUBLICATIONS

Klunk, W.E., et al., "Quantitative Evaluation of Congo Red Binding to Amyloid-like Proteins with a Beta-pleated Sheet Conformation," *J. Histochem. Cytochem.* 37:1273-1281, The Histochemical Society, Inc. (1989).

Klunk, W.E., et al, "Quantitative In Vitro NMR Analysis of Alzheimer's, Non-Alzheimer's Demented and Control Brain," *Biol. Psychiatry (Abstracts)* 35:627, Abstract No. 44., Elsevier (1994).

Klunk, W.E., et al., "Chrysamine-G Binding to Alzheimer and Control Brain: Autopsy Study of a New Amyloid Probe," *Neurobiol. Aging* 16:541-548, Elsevier Science Ltd. (1995).

Klunk, W.E., et al., "Staining of AD and Tg2576 Mouse Brain with X-34, a Highly Fluorescent Derivative of Chrysamine G and a Potential In Vivo Probe for β-sheet Fibrils," *Abstr. Soc. Neurosci.* 23:1638, Abstract No. 636.12, Society for Neuroscience (1997).

Kruijer, P.S., "Biodistribution of $^{123}$I-Labeled 4-Hydroxytamoxifen Derivatives in Rats with Dimethylbenzanthracene-Induced Mammary Carcinomas," *Nucl. Med. Biol.* 24:719-722, Elsevier Science Inc. (1997).

Kumari, N. et al., "Studies on Ylides Exclusive Formation of Olefins From Carbonyl Compounds on Treatment with *para*-Bromo- and *para*-Iodo-Benzylidenetriphenylarsenanes," *J. Organomet. Chem.* 96:237-241, Elsevier Sequoia S.A., Lausanne (1975).

Kuner, P. et al., "Controlling Polymerization of β-Amyloid and Prion-derived Peptides with Synthetic Small Molecule Ligands," *J. Biol. Chem.* 275:1673-1678, The American Society for Biochemistry and Molecular Biology, Inc. (2000).

Kung, H.F., "Novel Stilbenes as Probes for Amyloid Plaques," *J. Am. Chem. Soc.* 123:12740-12741, American Chemical Society (2001).

Lee, C-W. et al., "Isomerization of (Z,Z) to (E,E)1-Bromo-2,5-bis-(3- hydroxycarbonyl-4-hydroxy)-styrylbenzene in Strong Base: Probes for Amyloid Plaques in the Brain," *J. Med. Chem.* 44:2270-2275, American Chemical Society (2001).

Lorenzo, A., and Yankner, B.A., "β-Amyloid neurotoxicity requires fibril formation and is inhibited by Congo red," *Proc. Natl. Acad. Sci. USA* 91:12243-12247, National Academy Press (1994).

Mathis, C.A. et al., "Synthesis of a Lipophilic, Radioiodinated Ligand with High Affinity to Amyloid Protein in Alzheimer's Disease Brain Tissue," *J. Labelled Comp. Radiopharm.* 40:94-95, John Wiley & Sons, Ltd. (1997).

Moore, C.L. et al., "Difluoro Ketone Peptidomimetics Suggest a Large S1 Pocket for Alzheimer's γ-Secretase: Implications for Inhibitor Design," *J. Med. Chem.* 43:3434-3442, American Chemical Society (2000).

Näslund, J. et al, "Correlation Between Elevated Levels of Amyloid β-Peptide in the Brain and Cognitive Decline," *J. Am. Med. Assoc.* 283:1571-1577, American Medical Association (2000).

Selkoe, D.J. "Biology of β-Amyloid Precursor Protein and the Mechanism of Alzheimer Disease," in *Alzheimer Disease*, 2$^{nd}$ edition, Terry, R.D. et al., eds., Lippincott Williams & Wilkins, Philadelphia, PA, pp. 293-310 (1999).

Selkoe, D.J., "The Origins of Alzheimer Disease. A is for Amyloid," *J. Am. Med. Assoc.* 283:1615-1617, American Medical Association (2000).

Skovronsky, D.M., and Lee, V. M.-Y., "β-Secretase revealed: starting gate for race to novel therapies for Alzheimer's disease," *Trends Pharmacol. Sci.* 21:161-163, Elsevier (2000).

Vassar, R. et al., "β-Secretase Cleavage of Alzheimer's Amyloid Precursor Protein by the Transmembrane Aspartic Protease BACE," *Science* 286:735-741, American Association for the Advancement of Science (1999).

Vogelsberg-Ragaglia, V., et, al., "Cell Biology of Tau and Cytoskeletal Pathology in Alzheimer Disease," in *Alzheimer Disease*, 2$^{nd}$ edition, Terry, R.D. et al., eds., Lippincott Williams & Wilkins, Philadelphia, PA, pp. 359-372 (1999).

Wolfe, M.S. et al, "A Substrate-Based Difluoro Ketone Selectively Inhibits Alzheimer's γ-Secretase Activity," *J. Med. Chem.* 41:6-9, American Chemical Society (1998).

Xia, W. et al., "Presenilin complexes with the C-terminal fragments of amyloid precursor protein at the sites of amyloid β-protein generation," *Proc. Natl. Acad. Sci. USA* 97:9299-9304, National Academy of Sciences (2000).

Zhen, W. et al., "Synthesis and Amyloid Binding Properties of Rhenium Complexes: Preliminary Progress Toward a Reagent for Spect Imaging of Alzheimer's Disease Brain," *J. Med. Chem.* 42:2805-2815, American Chemical Society (1999).

Zhuang, Z.-P. et al., "Radioiodinated Styrylbenzenes and Thioflavins as Probes for Amyloid Aggregates," *J. Med. Chem.* 44:1905-1914, American Chemical Society (2001).

DatabaseCAPLUS, Chemical Abstracts Service, Accession No. 78:71798, Holand, S., et al., 1 page (1972).

Database CAPLUS, Chemical Abstracts Service, Accession No. 1976:73777, Tewari, R.S. et al., 1 page (1976).

Wermuth C G: "The Practice of Medicinal Chemistry, PASSAGE" Jan. 1, 1996, Practice of Medicinal Chemistry, XX, XX, pp. 756-776, XP002277818 * pp. 769-770, paragraph B.

Fialkov,Yu A. e al, "Transmission Of Electronic Effects In Conjugated Perfluoropropylene Systems" Journal Of Organic Chemistry USSR, vol. 14, 1978, pp. 939-946, XP009112014.

Kukhar, V. P.; Sagina, E. I.; Kirsanov, A. V.: "p-Dialkylaminobenzalkhloridy" Zhurnal Organicheskoi Khimii, vol. XI, No. 9, 1975, pp. 1922-1929, XP009112041.

Qibo, Liu, et al, "Stereoselective preparation of (E)-(1,2-difluoro-1,2-ethenediyl) bis[tributylstannane] and stereospecific synthesis of (E)-1,2-difluorostilbenes." Organic Letters May 2, 2002, vol. 4, No. 9, May 2, 2002, pp. 1483-1485, XP002514428 ISSN: 1523-7060.

Ruggli, Paul, "Über die Bildung eines zweifach kondensierten Indols" Berichte Der Deutschen Chemischen Gesellschaft, 1917, pp. 883-893, XP002514431.

Young, Han Sun, et al., "Design and synthesis of lignostilbene-alpha,beta-dioxygenase inhibitors." Bioorganic & Medicinal Chemistry Letters Apr. 22, 2002, vol. 12, No. 8, pp. 1139-1142, XP002514429 ISSN: 0960-894X.

Young, W.R.; Aviram, A.; Cox, R.J.; "Stilbene Derivatives. A New Class of Room Temperature Nematic Liquids" Journal Of The American Chemical Society, vol. 94, No. 11, 1972, pp. 3976-3981, XP002514430.

| q | $K_i$ (nM) |
|---|---|
| 2 | 2.9±0.2 |
| 3 | 6.7±0.3 |
| 4 | 4.4±0.8 |
| 5 | 6.8±0.8 |
| 6 | 7.5±1.5 |
| 7 | 8.7 |
| 8 | 9.0 | ns and their use for binding and imaging amyloid plaques

STILBENE DERIVATIVES AND THEIR USE FOR BINDING AND IMAGING AMYLOID PLAQUES

CROSS REFERENCE TO RELATED APPLICATIONS

This application claims the benefit of Provisional Application No. 60/636,696, filed Dec. 17, 2004, and 60/686,395, filed Jun. 2, 2005, the contents of which are entirely incorporated by reference herein.

Part of the work performed during development of this invention utilized U.S. Government funds. The U.S. Government has certain rights in this invention under grant number AG021868, awarded by the National Institutes of Health.

BACKGROUND OF THE INVENTION

1. Field of the Invention

This invention relates to novel bioactive compounds, methods of diagnostic imaging using radiolabeled compounds, and methods of making radiolabeled compounds.

2. Background Art

Alzheimer's disease (AD) is a progressive neurodegenerative disorder characterized by cognitive decline, irreversible memory loss, disorientation, and language impairment. Postmortem examination of AD brain sections reveals abundant senile plaques (SPs) composed of amyloid-β (Aβ) peptides and numerous neurofibrillary tangles (NFTs) formed by filaments of highly phosphorylated tau proteins (for recent reviews and additional citations see Ginsberg, S. D., et al., "Molecular Pathology of Alzheimer's Disease and Related Disorders," in *Cerebral Cortex: Neurodegenerative and Age-related Changes in Structure and Function of Cerebral Cortex*, Kluwer Academic/Plenum, NY (1999), pp. 603-654; Vogelsberg-Ragaglia, V., et al., "Cell Biology of Tau and Cytoskeletal Pathology in Alzheimer's Disease," *Alzheimer's Disease*, Lippincot, Williams & Wilkins, Philadelphia, Pa. (1999), pp. 359-372).

Amyloidosis is a condition characterized by the accumulation of various insoluble, fibrillar proteins in the tissues of a patient. An amyloid deposit is formed by the aggregation of amyloid proteins, followed by the further combination of aggregates and/or amyloid proteins. Formation and accumulation of aggregates of β-amyloid (Aβ) peptides in the brain are critical factors in the development and progression of AD.

In addition to the role of amyloid deposits in Alzheimer's disease, the presence of amyloid deposits has been shown in diseases such as Mediterranean fever, Muckle-Wells syndrome, idiopathic myeloma, amyloid polyneuropathy, amyloid cardiomyopathy, systemic senile amyloidosis, amyloid polyneuropathy, hereditary cerebral hemorrhage with amyloidosis, Down's syndrome, Scrapie, Creutzfeldt-Jacob disease, Kuru, Gerstamnn-Straussler-Scheinker syndrome, medullary carcinoma of the thyroid, Isolated atrial amyloid, $\beta_2$-microglobulin amyloid in dialysis patients, inclusion body myositis, $\beta_2$-amyloid deposits in muscle wasting disease, and Islets of Langerhans diabetes Type II insulinoma.

The fibrillar aggregates of amyloid peptides, $A\beta_{1-40}$ and $A\beta_{1-42}$, are major metabolic peptides derived from amyloid precursor protein found in senile plaques and cerebrovascular amyloid deposits in AD patients (Xia, W., et al., *J. Proc. Natl. Acad. Sci. U.S.A.* 97:9299-9304 (2000)). Prevention and reversal of Aβ plaque formation are being targeted as a treatment for this disease (Selkoe, D., J. JAMA 283:1615-1617 (2000); Wolfe, M. S., et al., J. Med. Chem. 41:6-9 (1998); Skovronsky, D. M., and Lee, V. M., *Trends Pharmacol. Sci.* 21:161-163 (2000)).

Familial AD (FAD) is caused by multiple mutations in the A precursor protein (APP), presenilin 1 (PS1) and presenilin 2 (PS2) genes (Ginsberg, S. D., et al., "Molecular Pathology of Alzheimer's Disease and Related Disorders," in *Cerebral Cortex: Neurodegenerative and Age-related Changes in Structure and Function of Cerebral Cortex*, Kluwer Academic/Plenum, NY (1999), pp. 603-654; Vogelsberg-Ragaglia, V., et al., "Cell Biology of Tau and Cytoskeletal Pathology in Alzheimer's Disease," *Alzheimer's Disease*, Lippincot, Williams & Wilkins, Philadelphia, Pa. (1999), pp. 359-372).

While the exact mechanisms underlying AD are not fully understood, all pathogenic FAD mutations studied thus far increase production of the more amyloidogenic 42-43 amino-acid long form of the Aβ peptide. Thus, at least in FAD, dysregulation of Aβ production appears to be sufficient to induce a cascade of events leading to neurodegeneration. Indeed, the amyloid cascade hypothesis suggests that formation of extracellular fibrillar Aβ aggregates in the brain may be a pivotal event in AD pathogenesis (Selkoe, D. J., "Biology of β-amyloid Precursor Protein and the Mechanism of Alzheimer's Disease," *Alzheimer's Disease*, Lippincot Williams & Wilkins, Philadelphia, Pa. (1999), pp. 293-310; Selkoe, D. J., *J. Am. Med. Assoc.* 283:1615-1617 (2000); Naslund, J., et al., *J. Am. Med. Assoc.* 283:1571-1577 (2000); Golde, T. E., et al., *Biochimica et Biophysica Acta* 1502:172-187 (2000)).

Various approaches in trying to inhibit the production and reduce the accumulation of fibrillar Aβ in the brain are currently being evaluated as potential therapies for AD (Skovronsky, D. M. and Lee, V. M., *Trends Pharmacol. Sci.* 21:161-163 (2000); Vassar, R., et al., *Science* 286:735-741 (1999); Wolfe, M. S., et al., *J. Med. Chem.* 41:6-9 (1998); Moore, C. L., et al., *J. Med. Chem.* 43:3434-3442 (2000); Findeis, M. A., *Biochimica et Biophysica Acta* 1502:76-84 (2000); Kuner, P., Bohrmann, et al., *J. Biol. Chem.* 275:1673-1678 (2000)). It is therefore of interest to develop ligands that specifically bind fibrillar Aβ aggregates. Since extracellular SPs are accessible targets, these new ligands could be used as in vivo diagnostic tools and as probes to visualize the progressive deposition of Aβ in studies of AD amyloidogenesis in living patients.

To this end, several interesting approaches for developing fibrillar Aβ aggregate-specific ligands have been reported (Ashburn, T. T., et al., *Chem. Biol.* 3:351-358 (1996); Han, G., et al., *J. Am. Chem. Soc.* 118:4506-4507 (1996); Klunk, W. E., et al., *Biol. Psychiatry* 35:627 (1994); Klunk, W. E., et al., *Neurobiol. Aging* 16:541-548 (1995); Klunk, W. E., et al., *Society for Neuroscience Abstract* 23:1638 (1997); Mathis, C. A., et al., *Proc. XIIth Intl. Symp. Radiopharm. Chem., Uppsala, Sweden*:94-95 (1997); Lorenzo, A. and Yankner, B. A., *Proc. Natl. Acad. Sci. U.S.A.* 91:12243-12247 (1994); Zhen, W., et al., *J. Med. Chem.* 42:2805-2815 (1999)). The most attractive approach is based on highly conjugated chrysamine-G (CG) and Congo red (CR), and the latter has been used for fluorescent staining of SPs and NFTs in postmortem AD brain sections (Ashburn, T. T., et al., *Chem. Biol.* 3:351-358 (1996); Klunk, W. E., et al., *J. Histochem. Cytochem.* 37:1273-1281 (1989)). The inhibition constants ($K_i$) for binding to fibrillar Aβ aggregates of CR, CG, and 3'-bromo- and 3'-iodo derivatives of CG are 2, 800, 370, 300 and 250 nM, respectively (Mathis, C. A., et al., *Proc. XIIth Intl. Symp. Radiopharm. Chem., Uppsala, Sweden*:94-95 (1997)). These compounds have been shown to bind selectively to Aβ (1-40) peptide aggregates in vitro as well as to fibrillar Aβ deposits in AD brain sections (Mathis, C. A., et al., *Proc. XIIth Intl. Symp. Radiopharm. Chem., Uppsala, Sweden*:94-95 (1997)).

There are several potential benefits of imaging Aβ aggregates in the brain. The imaging technique will improve diagnosis by identifying potential patients with excess Aβ plaques in the brain; therefore, they may be likely to develop Alzheimer's disease. It will also be useful to monitor the progression of the disease. When anti-plaque drug treatments become available, imaging Aβ plaques in the brain may provide an essential tool for monitoring treatment. Thus, a simple, noninvasive method for detecting and quantitating amyloid deposits in a patient has been eagerly sought. Presently, detection of amyloid deposits involves histological analysis of biopsy or autopsy materials. Both methods have drawbacks. For example, an autopsy can only be used for a postmortem diagnosis.

The direct imaging of amyloid deposits in vivo is difficult, as the deposits have many of the same physical properties (e.g., density and water content) as normal tissues. Attempts to image amyloid deposits using magnetic resonance imaging (MRI) and computer-assisted tomography (CAT) have been disappointing and have detected amyloid deposits only under certain favorable conditions. In addition, efforts to label amyloid deposits with antibodies, serum amyloid P protein, or other probe molecules have provided some selectivity on the periphery of tissues, but have provided for poor imaging of tissue interiors.

Potential ligands for detecting Aβ aggregates in the living brain must cross the intact blood-brain barrier. Thus brain uptake can be improved by using ligands with relatively smaller molecular size (compared to Congo Red) and increased lipophilicity. Highly conjugated thioflavins (S and T) are commonly used as dyes for staining the Aβ aggregates in the AD brain (Elhaddaoui, A., et al., *Biospectroscopy* 1:351-356 (1995)).

A highly lipophilic tracer, [$^{18}$F]FDDNP, for binding both tangles (mainly composed of hyperphosphorylated tau protein) and plaques (containing Aβ protein aggregates) has been reported. (Shoghi-Jadid K, et al., *Am J Geriatr Psychiatry*. 2002; 10:24-35). Using positron-emission tomography (PET), it was reported that this tracer specifically labeled deposits of plaques and tangles in nine AD patients and seven comparison subjects. (Nordberg A. *Lancet Neurol.* 2004; 3:519-27). Using a novel pharmacokinetic analysis procedure called the relative residence time of the brain region of interest versus the pons, differences between AD patients and comparison subjects were demonstrated. The relative residence time was significantly higher in AD patients. This is further complicated by an intriguing finding that FDDNP competes with some NSAIDs for binding to Aβ fibrils in vitro and to Aβ plaques ex vivo (Agdeppa E D, et al. 2001; Agdeppa E D, et al., *Neuroscience*. 2003; 117:723-30).

Imaging β-amyloid in the brain of AD patients by using a benzothiazole aniline derivative, [$^{11}$C]6-OH-BTA-1 (also referred to as [$^{11}$C]PIB), was recently reported. (Mathis Calif., et al., *Curr Pharm Des*. 2004; 10:1469-92; Mathis Calif., et al., *Arch. Neurol.* 2005, 62:196-200). Contrary to that observed for [$^{18}$F]FDDNP, [$^{11}$C]6-OH-BTA-1 binds specifically to fibrillar Aβ in vivo. Patients with diagnosed mild AD showed marked retention of [$^{11}$C]6-OH-BTA-1 in the cortex, known to contain large amounts of amyloid deposits in AD. In the AD patient group, [$^{11}$C]6-OH-BTA-1 retention was increased most prominently in the frontal cortex. Large increases also were observed in parietal, temporal, and occipital cortices and in the striatum. [$^{11}$C]6-OH-BTA-1 retention was equivalent in AD patients and comparison subjects in areas known to be relatively unaffected by amyloid deposition (such as subcortical white matter, pons, and cerebellum). Recently, another $^{11}$C labeled A: plaque-targeting probe, a stilbene derivative-[$^{11}$C]SB-13, has been studied. In vitro binding using the [$^{3}$H]SB-13 suggests that the compound showed excellent binding affinity and binding can be clearly measured in the cortical gray matter, but not in the white matter of AD cases. (Kung M-P, et al., *Brain Res.* 2004; 1025:98-105. There was a very low specific binding in cortical tissue homogenates of control brains. The Kd values of [$^{3}$H]SB-13 in AD cortical homogenates were 2.4±0.2 nM. High binding capacity and comparable values were observed (14-45 pmol/mg protein) (Id.). As expected, in AD patients [$^{11}$C]SB-13 displayed a high accumulation in the frontal cortex (presumably an area containing a high density of Aβ plaques) in mild to moderate AD patients, but not in age-matched control subjects. (Verhoeff N P, et al., *Am J Geriatr Psychiatry.* 2004; 12:584-95).

It would be useful to have a noninvasive technique for imaging and quantitating amyloid deposits in a patient. In addition, it would be useful to have compounds that inhibit the aggregation of amyloid proteins to form amyloid deposits and a method for determining a compound's ability to inhibit amyloid protein aggregation.

SUMMARY OF THE INVENTION

The present invention provides novel compounds of Formulae I, II and III.

The present invention also provides diagnostic compositions comprising a radiolabeled compound of Formula I, II or III and a pharmaceutically acceptable carrier or diluent.

The invention further provides a method of imaging amyloid depositis, the method comprising introducing into a patient a detectable quantity of a labeled compound of Formula I, II or III or a pharmaceutically acceptable salt, ester, amide or prodrug thereof.

The present invention also provides a method for inhibiting the aggregation of amyloid proteins, the method comprising administering to a mammal an amyloid inhibiting amount of a compound Formula I, II or III or a pharmaceutically acceptable salt, ester, amide, or prodrug thereof.

A further aspect of this invention is directed to methods and intermediates useful for synthesizing the amyloid inhibiting and imaging compounds of Formula I, II or III described herein.

DETAILED DESCRIPTION OF THE INVENTION

Figure 1:
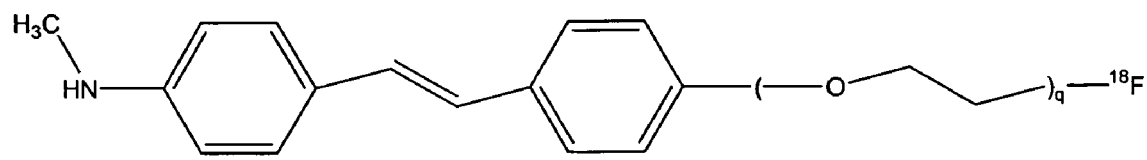
FIG. 1 depicts $K_i$ binding data of several compounds of the present invention.

In a first aspect the present invention is directed to compounds of Formula I:

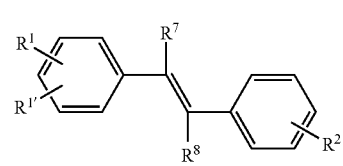

I or a pharmaceutically acceptable salt or prodrug thereof, wherein:

$R^1$ is selected from the group consisting of:
a. $NR^aR^b$, wherein $R^a$ and $R^b$ are independently hydrogen, $C_{1-4}$ alkyl, $(CH_2)d^{18}F$, and d is an integer between 1 and 4,
b. hydroxy,
c. $C_{1-4}$ alkoxy,
d. hydroxy($C_{1-4}$)alkyl,
e. halogen,
f. cyano,
g. hydrogen,
h. nitro,
i. $(C_1-C_4)$alkyl,
j. Halo$(C_1-C_4)$alkyl, and
k. formyl $R^{1'}$ is selected from the group consisting of
a. $^{123}I$, $^{125}I$, $^{131}I$, $^{18}F$, $^{76}Br$;
b. hydrogen
c. $^{18}F(C_{1-4})$alkyl,
d. [$^{18}F(C_{1-4})$alkyl]amino,
e. [$^{18}F(C_1-C_4)$alkyl]alkylamino
f. $^{18}F(C_1-C_4)$alkoxy $R^2$ is selected from the group consisting of
i. hydroxyl, $C_{1-4}$Alkoxy, $(C_1-C_4)$-alkyloxoAlk$(C_1-C_4)$oxy, $(C_1-C_4)$-alkyloxo$(C_1-C_4)$-alkyloxo$(C_1-C_4)$alkoxy, $(C_1-C_4)$-alkyloxo$(C_1-C_4)$-alkyloxo$(C_1-C_4)$-alkyloxo$(C_1-C_4)$alkoxy, carboxy$(C_1-C_4)$Alkyl, halo$(C_1-C_4)$alkoxy, halo$(C_1-C_4)$-alkyloxo$(C_1-C_4)$alkoxy, halo$(C_1-C_4)$alkyloxo$(C_1-C_4)$alkyloxo$(C_1-C_4)$-alkyloxy, halo$(C_1-C_4)$alkyloxo$(C_1-C_4)$alkyloxo$(C_1-C_4)$alkyloxo$(C_1-C_4)$alkyloxy, halo$(C_1-C_4)$alkyl, $NR^6R^{6'}$, phenyl$(C_1-C_4)$alkyl, $^{18}F(C_1-C_4)$alkoxy, $^{18}F(C_1-C_4)$alkyloxo$(C_1-C_4)$alkoxy, $^{18}F(C_1-C_4)$alkyloxo$(C_1-C_4)$alkyloxo$(C_1-C_4)$alkyloxy, $^{18}F(C_1-C_4)$alkyloxo$(C_1-C_4)$alkyloxo$(C_1-C_4)$alkyloxo$(C_1-C_4)$alkyloxy, $^{18}F(C_1-C_4)$alkyl, wherein $R^6$ and $R^{6'}$ are independently selected from the group consisting of hydrogen, hydroxy$(C_1-C_4)$alkyl and $C_1-C_4$alkyl ii.

where q is an integer from one to 10; Z is selected from the group consisting of $^{18}F$, $^{18}F$ substituted benzoyloxy, $^{18}F$ substituted benzyloxy, preferably $^{18}F$-phenoxy, $^{18}F$ substituted phenyl$(C_{1-4})$alkyl, $^{18}F$ substituted $(C_{1-4})$alkoxy, $^{18}F$ substituted aryloxy and a $^{18}F$ substituted $C_{6-10}$ aryl, preferably $^{18}F$-phenyl; and $R^{30}$, $R^{31}$, $R^{32}$ and $R^{33}$ are in each instance independently selected from the group consisting of hydrogen, hydroxy, $C_{1-4}$ alkoxy, $C_{1-4}$ alkyl, and hydroxy$(C_{1-4})$alkyl;

iii.

wherein Z, $R^{30}$, $R^{31}$, $R^{32}$ and $R^{33}$ are as described above;

iv.

where Y is selected from the group consisting of $^{18}F$, $^{18}F$ substituted benzoyloxy, $^{18}F$ substituted phenyl$(C_{1-4})$alkyl, $^{18}F$ substituted aryloxy preferably $^{18}F$-phenoxy and $^{18}F$ substituted $C_{60-10}$ aryl, preferably $^{18}F$-phenyl;

U is selected from the group consisting of hydrogen, hydroxy, $^{18}F$, $^{18}F$ substituted benzoyloxy, $^{18}F$ substituted phenyl$(C_{1-4})$alkyl, $^{18}F$ substituted aryloxy, preferably $^{18}F$-phenoxy and $^{18}F$ substituted $C_{6-10}$ aryl, preferably $^{18}F$-phenyl; and $R^{34}$, $R^{35}$, $R^{36}$, $R^{37}$, $R^{38}$, $R^{39}$ and $R^{40}$ are in each instance independently selected from the group consisting of hydrogen, hydroxy, $C_{1-4}$ alkoxy, $C_{1-4}$ alkyl, and hydroxy$(C_{1-4})$alkyl; and $R^7$ and $R^8$ are in each instance independently selected from the group consisting of halogen, e.g. F, Cl, Br, hydrogen, hydroxy, amino, methylamino, dimethylamino, $C_{1-4}$ alkoxy, $C_{1-4}$ alkyl, and hydroxy$(C_{1-4})$alkyl, wherein at least one of $R^7$ and $R^8$ is halogen, preferably F.

In a preferred embodiment $R^1$ is independently selected from the group consisting of hydrogen, halogen, e.g. F, Cl, Br, $C_1-C_4$ alkyl, cyano, hydroxyl, nitro, $(C_1-C_4)$alkylamino, di$(C_1-C_4)$alkylamino, halo$(C_1-C_4)$alkyl, formyl, and alk$(C_1-C_4)$-oxy $R^{1'}$ is independently selected from thr group consisting of hydrogen, $^{123}I$, $^{125}I$, $^{131}I$, $^{18}F$, $^{18}F(C_{1-4})$alkyl, [$^{18}F(C_{1-4})$alkyl]amino, [$^{18}F(C_1-C_4)$alkyl]alkylamino, $^{18}F(C_1-C_4)$alkoxy and $^{76}Br$ $R^2$ is independently selected from the group consisting of hydroxyl, $C_{1-4}$alkoxy, $(C_1-C_4)$alkyloxoalk$(C_1-C_4)$oxy, carboxy$(C_1-C_4)$alkyl, halo$(C_1-C_4)$alkoxy, halo$(C_1-C_4)$alkyloxo $(C_1-C_4)$alkoxy, Halo$(C_1-C_4)$alkyloxo$(C_1-C_4)$-$(C_1-C_4)$alkyloxy, halo$(C_1-C_4)$alkyloxo$(C_1-C_4)$alkyloxo$(C_1-C_4)$ alkyloxo-$(C_1-C_4)$alkyloxy, halo$(C_1-C_4)$alkyl, $NR^6R^{6'}$, phenyl$(C_1-C_4)$alkyl, $^{18}F(C_1-C_4)$alkoxy, $^{18}F(C_1-C_4)$alkyloxo-$(C_1-C_4)$alkoxy, $^{18}F(C_1-C_4)$alkyloxo-$(C_1-C_4)$-alkyloxo$(C_1-C_4)$alkyloxy, $^{18}F(C_1-C_4)$alkyloxo$(C_1-C_4)$alkyloxo$(C_1-C_4)$ alkyloxo-$(C_1-C_4)$alkyloxy, $^{18}F(C_1-C_4)$alkyl $R^6$ and $R^{6'}$ are independently selected from the group consisting of hydrogen, hydroxy$(C_1-C_4)$alkyl, and $C_1-C_4$alkyl, $R^7$ and $R^8$ is selected from H, F, Cl or Br, wherein either $R^7$ and $R^8$ is halogen.

In a further preferred embodiment $R^1$ is selected from the group consisting of hydrogen, hydroxy, $(C_1-C_4)$alkylamino, di$(C_1-C_4)$alkylamino, methyl and methoxy, in particular from hydrogen, methylamino, and dimethylamino, $R^{1'}$ is selected from the group consisting of hydrogen, $^{123}I$, $^{125}I$, $^{131}I$ and $^{18}F$, in particular from hydrogen, $R^2$ is selected from the group consisting of hydroxy, $C_1-C_4$alkoxy, $NR^6R^{6'}$, $^{18}F$ $(C_1-C_4)$alkoxy, $^{18}F(C_1-C_4)$alkyloxo$(C_1-C_4)$alkoxy, $^{18}F(C_1-C_4)$alkyloxo$(C_1-C_4)$alkyloxo$(C_1-C_4)$alkyloxy, $^{18}F(C_1-C_4)$alkyloxo$(C_1-C_4)$alkyloxo-$(C_1-C_4)$alkyloxo$(C_1-C_4)$alkyloxy, $^{18}F(C_1-C_4)$alkyl, in particular from $(C_1-C_4)$alkyloxo$(C_1-C_4)$alkoxy, $^{18}F(C_1-C_4)$alkyloxo$(C_1-C_4)$alkyloxo$(C_1-C_4)$alkyloxy, and $^{18}F(C_1-C_4)$alkyloxo$(C_1-C_4)$alkyloxo$(C_1-C_4)$alkyloxo$(C_1-C_4)$alkyloxy, $R^6$ and $R^{6'}$ are independently selected from the group consisting of hydrogen, hydroxy$(C_1-C_4)$alkyl and $C_1-C_4$alkyl, $R^7$ und $R^8$ is selected from the group consisting of hydrogen and fluorine, wherein either $R^7$ or $R^8$ is fluorine.

It has been surprisingly found that stilbene derivatives which carry an additional halogen, in particular, fluorine atom at the double bond show improved pharmacokinetic properties and/or an increased metabolic stability and/or an increased geometrically isomeric stability and uniformity.

Preferred compounds of Formula I have the following structures:

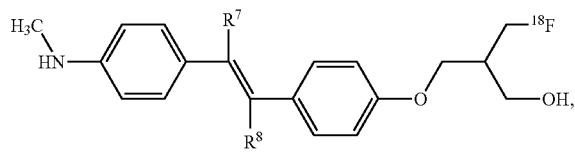

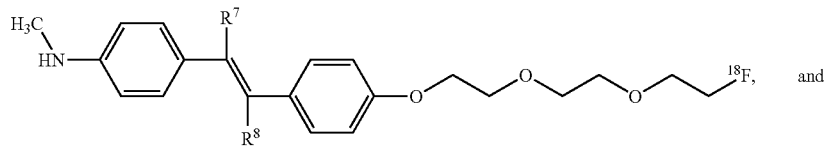
and

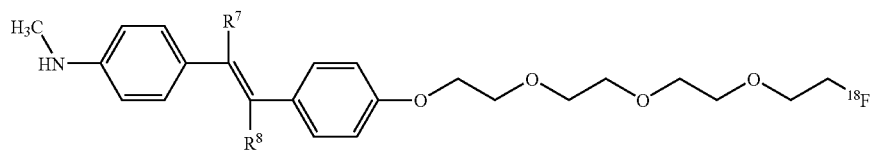

wherein one of $R^7$ and $R^8$ is hydrogen, and the other is halogen.

A second aspect of the present invention is directed to compounds of Formula II:

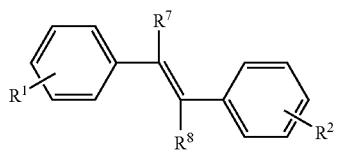

II or a pharmaceutically acceptable salt thereof, wherein:
$R^1$ is selected from the group consisting of:
 a. $NR^aR^b$, wherein $R^a$ and $R^b$ are independently hydrogen, $C_{1-4}$ alkyl, $(CH_2)_d{}^{18}F$, and d is an integer between 1 and 4, or $R^a$ and $R^b$ are both oxygen to form a nitro,
 b. hydroxy,
 c. $C_{1-4}$alkoxy, and
 d. hydroxy($C_{1-4}$)alkyl;
$R^2$ is selected from the group consisting of:

i.

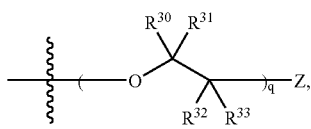

where q is an integer from one to 10; Z is selected from the group consisting of $^{18}F$, $^{18}F$ substituted benzoyloxy, $^{18}F$ substituted ($C_{1-4}$)alkoxy, $^{18}F$ substituted benzyloxy, preferably $^{18}F$-phenoxy, $^{18}F$ substituted phenyl($C_{1-4}$)alkyl, $^{18}F$ substituted aryloxy, and a $^{18}F$ substituted $C_{6-10}$ aryl, preferably $^{18}F$-phenyl; and $R^{30}$, $R^{31}$, $R^{32}$ and $R^{33}$ are in each instance independently selected from the group consisting of hydrogen, hydroxy, $C_{1-4}$ alkoxy, $C_{1-4}$ alkyl and hydroxy($C_{1-4}$)alkyl;

ii.

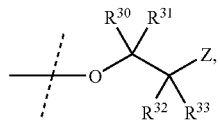

wherein Z, $R^{30}$, $R^{31}$, $R^{32}$ and $R^{33}$ are as described above;

iii.

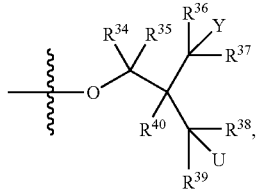

where Y is selected from the group consisting of $^{18}F$, $^{18}F$ substituted benzoyloxy, $^{18}F$ substituted phenyl($C_{1-4}$)alkyl, $^{18}F$ substituted aryloxy, preferably $^{18}F$-phenoxy, and $^{18}F$ substituted $C_{6-10}$ aryl, preferably $^{18}F$-phenyl;

U is selected from the group consisting of hydrogen, hydroxy, $^{18}F$, $^{18}F$ substituted benzoyloxy, $^{18}F$ substituted phenyl($C_{1-4}$)alkyl, $^{18}F$ substituted aryloxy, preferably $^{18}F$-phenoxy and $^{18}F$ substituted $C_{6-10}$ aryl, preferably $^{18}F$-phenyl; and $R^{34}$, $R^{35}$, $R^{36}$, $R^{37}$, $R^{38}$, $R^{39}$ and $R^{40}$ are in each instance independently selected from the group consisting of hydrogen, hydroxy, $C_{1-4}$ alkoxy, $C_{1-4}$ alkyl, and hydroxy($C_{1-4}$) alkyl; and $R^7$ and $R^8$ are in each instance independently selected from the group consisting of hydrogen, hydroxy, amino, methylamino, dimethylamino, $C_{1-4}$ alkoxy, $C_{1-4}$ alkyl, and hydroxy ($C_{1-4}$)alkyl.

More preferably, the value of each of $R^{30}$, $R^{31}$, $R^{32}$, $R^{33}$, $R^{34}$, $R^{35}$, $R^{36}$, $R^{37}$, $R^{38}$, $R^{39}$ and $R^{40}$ is in each instance independently selected from the group consisting of hydrogen, hydroxy, amino, methylamino, dimethylamino and methoxy.

Preferably, $R^2$ is either in the meta or para position relative to the ethylene bridge.

When $R^2$ is i.

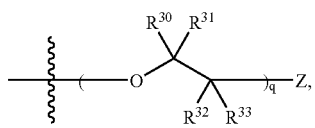

the preferred value for $R^{30}$, $R^{31}$, $R^{32}$ and $R^{33}$ in each instance is hydrogen, and Z is $^{18}F$. Useful values of q include integers from one to ten. Preferably, q is an integer from 2 to 5. More preferably, the value of q is 3 or 4.

Preferred embodiments of Formula II include the following structures wherein $R^a$ and $R^b$ are independently hydrogen or methyl, preferably at least one of $R^a$ and $R^b$ is methyl:

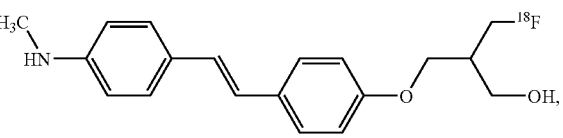

and X is $^{18}F$.

A preferred series of compounds of Formula II include $^{18}F$ labeled polyethyleneglycol(PEG)-stilbene derivatives having the following structures:

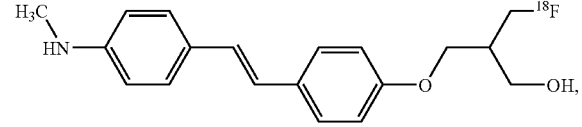

-continued

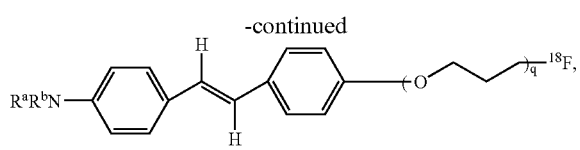

wherein, q is an integer from one to ten. More preferred compounds include those where q is equal to:

two,

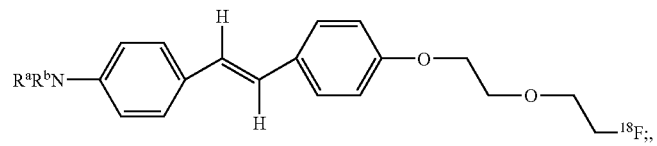

three,

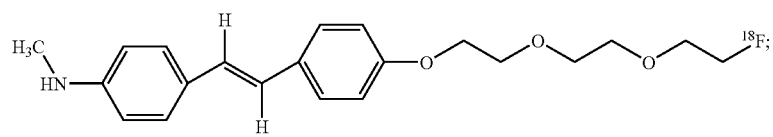

or four,

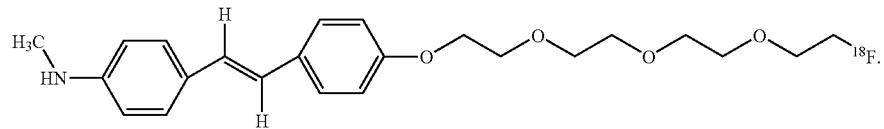

In this series of compounds, $^{18}$F is linked to the stilbene through a PEG chain, having a variable number of ethoxy groups. All of the fluorinated stilbenes displayed high binding affinities in an assay using postmortem AD brain homogenates ($K_i$=2.9-6.7 nM). As shown in Schemes 1-3 herein, radiolabeling was successfully performed by a substitution of the mesylate group of 10a-d by [$^{18}$F]fluoride giving the target compounds [$^{18}$F]12a-d (EOS, specific activity, 900-1,500 Ci/mmol; radiochemical purity >99%). In vivo biodistribution of these $^{18}$F ligands in normal mice exhibited excellent brain penetrations and rapid washouts after an iv injection (6.6-8.1 and 1.2-2.6% dose/g at 2 min and 60 min, respectively). Autoradiography of postmortem AD brain sections of [$^{18}$F]12a-d confirmed the specific binding related to the presence of Aβ plaques. In addition, in vivo plaque labeling can be clearly demonstrated with these $^{18}$F labeled agents in transgenic mice (Tg2576), a useful animal model for Alzheimer's disease.

The present invention is also directed to compounds of Formula III:

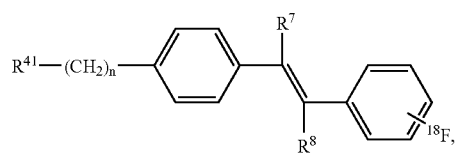

wherein n is an integer between 1 and 4, $R^7$ and $R^8$ are each as described above, and $R^{41}$ is selected from the group consisting of hydroxy and $NR^aR^b$, wherein $R^a$ and $R^b$ are independently hydrogen, $C_{1-4}$ alkyl or $R^a$ and $R^b$ are both oxygen to form a nitro.

Preferably, n is one, and $R^{41}$ is hydroxy, methylamino or dimethylamino.

Preferable values under the scope of $C_{6-10}$ aryl include phenyl, naphthyl or tetrahydronaphthyl. Preferable values of under the scope of heteroaryl include thienyl, furyl, pyranyl, pyrrolyl, pyridinyl, indolyl, and imidazolyl. Preferable values under the scope of heterocycle include piperidinyl, pyrrolidinyl, and morpholinyl.

The compounds of Formulae I, II and III may also be solvated, especially hydrated. Hydration may occur during manufacturing of the compounds or compositions comprising the compounds, or the hydration may occur over time due to the hygroscopic nature of the compounds. In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

It is also to be understood that the present invention is considered to include stereoisomers, such as both cis and trans isomers of the stilbene-type compounds. Further included are: optical isomers, e.g. mixtures of enantiomers as well as individual enantiomers and diastereomers, which arise as a consequence of structural asymmetry in selected compounds of Formula I, II or III.

When any variable occurs more than one time in any constituent or in Formula I, II or III its definition on each occurrence is independent of its definition at every other occurrence. Also combinations of substituents and/or variables are permissible only if such combinations result in stable compounds.

The term "alkyl" as employed herein by itself or as part of another group refers to both straight and branched chain radicals of up to 8 carbons, preferably 6 carbons, more preferably 4 carbons, such as methyl, ethyl, propyl, isopropyl, butyl, t-butyl, and isobutyl.

The term "alkoxy" is used herein to mean a straight or branched chain alkyl radical, as defined above, unless the chain length is limited thereto, bonded to an oxygen atom, including, but not limited to, methoxy, ethoxy, n-propoxy, isopropoxy, and the like. Preferably the alkoxy chain is 1 to 6 carbon atoms in length, more preferably 1-4 carbon atoms in length.

The term "monoalkylamine" as employed herein by itself or as part of another group refers to an amino group which is substituted with one alkyl group as defined above.

The term "dialkylamine" as employed herein by itself or as part of another group refers to an amino group which is substituted with two alkyl groups as defined above.

The term "halo" or "halogen" employed herein by itself or as part of another group refers to chlorine, bromine, fluorine or iodine, unless defined otherwise in specific uses in the text and/or claims.

The term "haloalkyl" as employed herein refers to any of the above alkyl groups substituted by one or more chlorine, bromine, fluorine or iodine with fluorine and chlorine being preferred, such as chloromethyl, iodomethyl, trifluoromethyl, 2,2,2-trifluoroethyl, and 2-chloroethyl.

The term "aryl" as employed herein by itself or as part of another group refers to monocyclic or bicyclic aromatic groups containing from 6 to 12 carbons in the ring portion, preferably 6-10 carbons in the ring portion, such as phenyl, naphthyl or tetrahydronaphthyl.

The term "heterocycle" or "heterocyclic ring", as used herein except where noted, represents a stable 5- to 7-membered mono-heterocyclic ring system which may be saturated or unsaturated, and which consists of carbon atoms and from one to three heteroatoms selected from the group consisting of N, O, and S, and wherein the nitrogen and sulfur heteroatom may optionally be oxidized. Especially useful are rings contain one nitrogen combined with one oxygen or sulfur, or two nitrogen heteroatoms. Examples of such heterocyclic groups include piperidinyl, pyrrolyl, pyrrolidinyl, imidazolyl, imidazinyl, imidazolidinyl, pyridyl, pyrazinyl, pyrimidinyl, oxazolyl, oxazolidinyl, isoxazolyl, isoxazolidinyl, thiazolyl, thiazolidinyl, isothiazolyl, homopiperidinyl, homopiperazinyl, pyridazinyl, pyrazolyl, and pyrazolidinyl, most preferably thiamorpholinyl, piperazinyl, and morpholinyl.

The term "heteroatom" is used herein to mean an oxygen atom ("O"), a sulfur atom ("S") or a nitrogen atom ("N"). It will be recognized that when the heteroatom is nitrogen, it may form an $NR^aR^b$ moiety, wherein $R^a$ and $R^b$ are, independently from one another, hydrogen or $C_{1-4}$ alkyl, $C_{24}$ aminoalkyl, $C_{1-4}$ halo alkyl, halo benzyl, or $R^1$ and $R^2$ are taken together to form a 5- to 7-member heterocyclic ring optionally having O, S or $NR^c$ in said ring, where $R^c$ is hydrogen or $C_{1-4}$ alkyl.

The term "heteroaryl" as employed herein refers to groups having 5 to 14 ring atoms; 6, 10 or 14 Π electrons shared in a cyclic array; and containing carbon atoms and 1, 2, 3 or 4 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4aH-carbazolyl, carbazolyl, Ǝ-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The term "aralkyl" or "arylalkyl" as employed herein by itself or as part of another group refers to $C_{1-6}$alkyl groups as discussed above having an aryl substituent, such as benzyl, phenylethyl or 2-naphthylmethyl.

The present invention is further directed to methods of preparing compounds of the above Formula I, II or III. The compounds of this invention can be prepared by reactions described in schemes 1-8.

Scheme 1 depicts a synthetic route for forming thiophene containing derivatives of Formula I, specifically certain Formula Ia compounds.

The fluorinated PEG stilbenes 12a-d were prepared by reactions shown in scheme 1. To prepare compounds with 2 or 3 ethoxy groups as the PEG linkage, commercially available chlorides 2a,b were coupled with the OH group of 4-methylamino-4'-hydroxy stilbene, 1 (Ono M, et al., *Nucl Med Biol.* 2003; 30:565-71; Wilson A, et al., *J Labelled Cpd Radiopharm.* 2003; 46:S61) to obtain 3a,b respectively. The free OH groups of 3a,b were subsequently protected with TBDMSCl to give compounds 7a,b. To prepare compounds with 4 or 5 ethoxy groups as the PEG linkage, bromides 6c,d were separately prepared as shown in scheme 2 and then coupled with stilbene 1 to give TBS protected compounds 7c,d. The O-TBS protecting groups on compounds 7c,d were removed by treatment of TBAF (1M) in THF to give 3c,d. Compounds 8a-d were obtained by protecting the methylamino groups of 7a-d with BOC. After removing the TBS protection groups of 8a-d with TBAF (1M)/THF, the free OH groups were converted into mesylates by reacting with MsCl in the present of triethylamine to give 10a-d. The "cold" fluorinated PEG stilbenes, 12a-d, were successfully obtained by refluxing 10a-d in anhydrous TBAF/THF (Cox D P, et al., *J Org Chem.* 1984; 49:3216-19) followed by stirring with TFA to remove the BOC protection group.

To make the desired $^{18}$F labeled PEG stilbenes, [$^{18}$F]12a-d, the N-BOC protected mesylates 10a-d were employed as the precursors (Scheme 3). Each of the mesylates, 10a-d, was mixed with [$^{18}$F]fluoride/potassium carbonate and Kryptofix 222 in DMSO and heated at 120° C. for 4 min. The mixture was then treated with aqueous HCl to remove the N-BOC protecting group. The crude product was purified by HPLC (radiochemical purity>99%, radiochemical yield 10-30%, decay corrected). The preparation of each $^{18}$F labeled compound, [$^{18}$F]12a-d, took about 90 min and the specific activity was estimated to be 900-1,500 Ci/mmol at the end of synthesis.

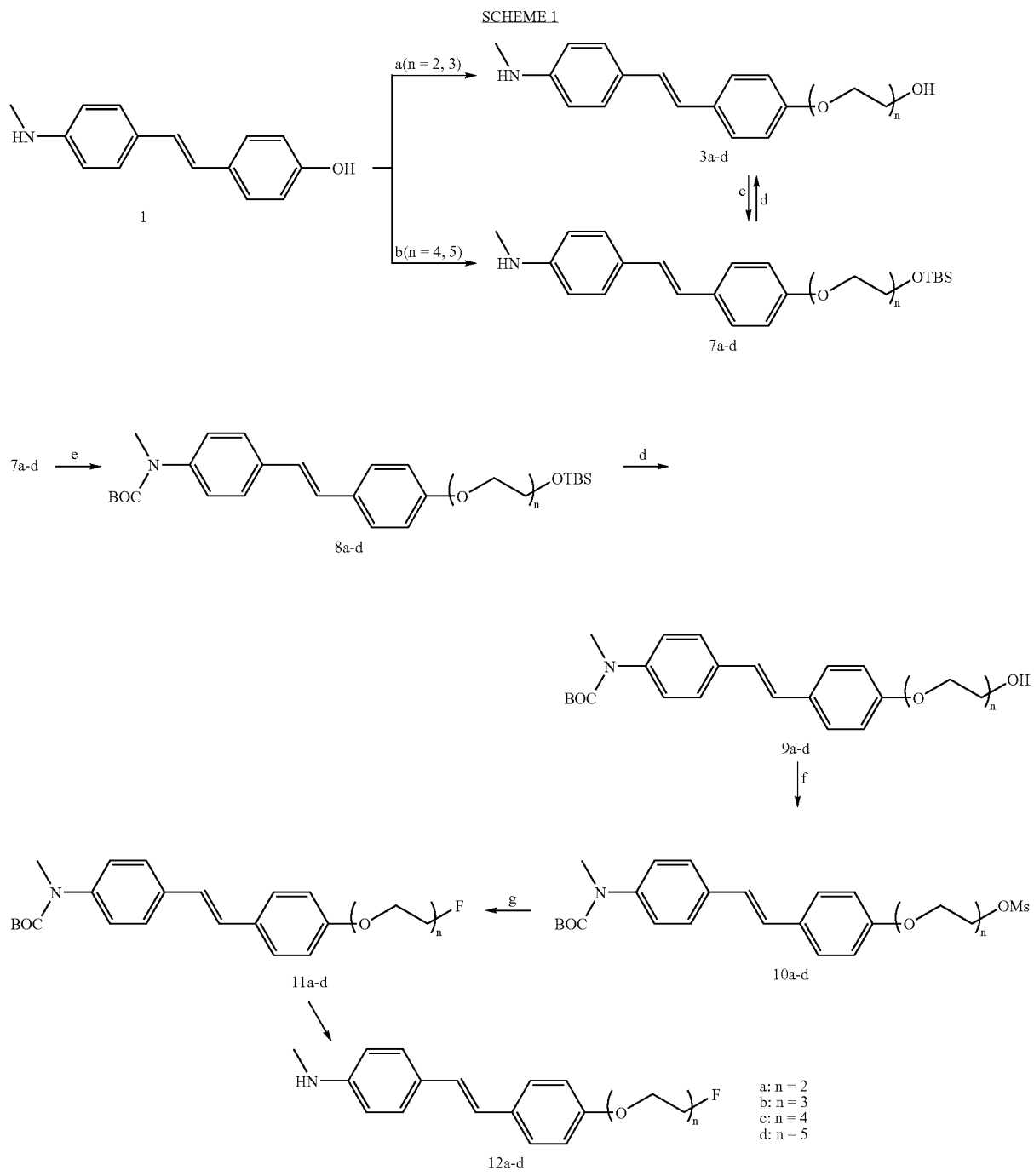

SCHEME 2

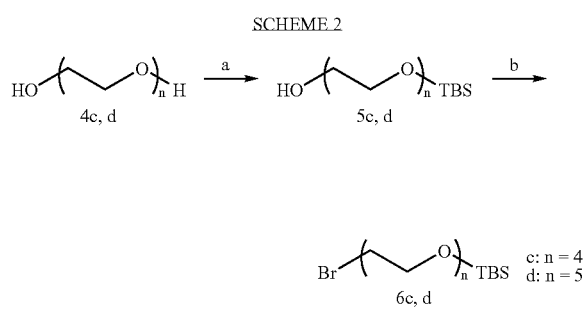

Scheme 2
a TBSCl, Et₃N, DCM;
b CBr₄, PPh₃, DCM

SCHEME 3

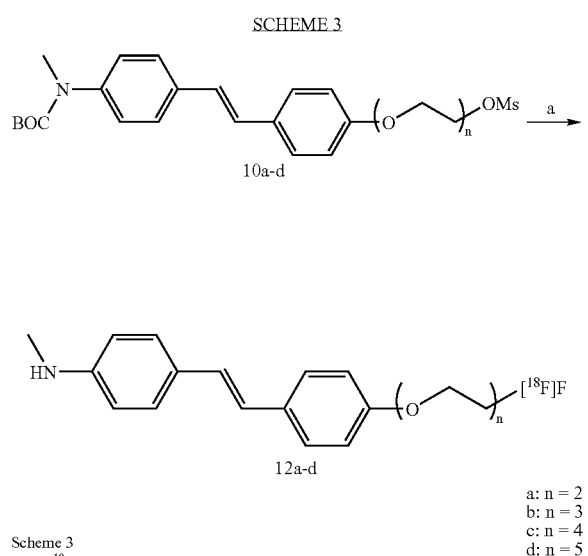

Scheme 3
a 1) [$^{18}$F]F⁻/K222, K₂CO₃, DMSO; 2) HCl aq

The syntheses of compounds 15e, 16e and the syntheses of the radiolabeling precursors 15d, 17d for preparing [$^{18}$F]15e and [$^{18}$F]6e are shown in Scheme 9. To prepare compound 15a, the nitro group of 4-nitro-4'-hydroxy stilbene, 13a, was reduced with SnCl₂ in ethanol to give the corresponding amine 14a. The amino group was then treated with (CHO)$_n$ and NaBH₃CN to give the dimethylamino compound 15a. Compound 15b was obtained by reacting the hydroxyl stilbene, 15a, with bromide 20m (which was separately prepared as shown in Scheme 10) and potassium carbonate in anhydrous DMF. Compound 15c was obtained by the treatment of 15b with 1N HCl in acetone. Mono tosylate 15d could be isolated from a product mixture of reacting diol 15c with 1.5 equivalent of tosyl chloride in pyridine. The tosylate 15d was converted into floride 15e by refluxing with anhydrous TBAF in THF. TBAF has to be dried at 58° C. under high vacuum (<0.5 mmHg) for 24 hr before use. The tosyl compound 15d was used as the starting material to obtain radio labeled compound [$^{18}$F]15e. Nitro compound 13e was similarly synthesized by a coupling reaction of 13a with 20m followed by tosylation and fluorination. The synthesis of compound 16e was accomplished by the reduction of the nitro group of 13e with SnCl₂/EtOH followed by the monomethylation of the amino group with (CHO)$_n$, NaOCH₃ and NaBH₄. An intermediate, 13b, was reduced to amine, 14c, and then monomethylated to give compound 16c. To obtain [$^{18}$F]16e, N-protected tosylate 17d was designed as the precursor for radiolabeling, Previously prepared 14a was first monomethylated to 16a. The compound 17f was then prepared by coupling of 16a with 20n (Scheme 10) and the introduction of BOC to the 2° amine. Di-tert-butyl siliyl group of 17f was removed with 1N TBAF in THF at room temperature to give diol 5c, which was monotosylated to yield compound 17d.

A related compound 15h was also synthesized as shown in Scheme 4. The substituted malonate 21 was reduced to diol 22 with DIBALH and then reacted with one equivalent of TBSCl to give 23. The unprotected OH was then converted into bromide 24 with CBr₄/PPh₃. Compound 24 was reacted with 15a to give 15g which was treated with TBAF to remove TBS group to yield 15h.

Two benzyl derivatives of N,N-dimethyl stilbene, 14 and 15 were also synthesized (Scheme 4). Compound 14 was obtained by the reduction of the corresponding ethyl ester 133 with LiAlH₄. The benzyl alcohol was then converted into the highly reactive benzyl bromide intermediate with HBr/HOAc, which was, without purofication, converted immediately into methyl ether 15 by the addition of methanol and potassium carbonate.

Those stilbene derivatives with a fluorine atom being directly attached to the double bond (Formula I: R⁷ or R⁸ is fluorine) were synthesized by well known methods (e.g. Tetrahedron Lett. 43, (2002), 2877-2879).

To obtain [$^{18}$F]15e, precursor 15d was mixed with [$^{18}$F] fluoride/potassium carbonate and Kryptofix® 222 in DMSO and heated at 120° C. for 4 min. Crude product was purified by HPLC to attain >99% of the radiochemical purity with 10% radiochemical yield (decay corrected). The procedure took 90 min and specific activity was estimated to be 70 Ci/mmol at the end of synthesis. The similar procedure was carried out to obtain [$^{18}$F]16e from precursor 17d. After initial reaction in DMSO, the mixture was treated with aqueous HCl to remove BOC group. Radiochemical purity was >99% after HPLC purification and the radiochemical yield was 15%. The total synthesis took 110 min and specific activity was estimated to be 90 Ci/mmol at the end of synthesis.

SCHEME 4
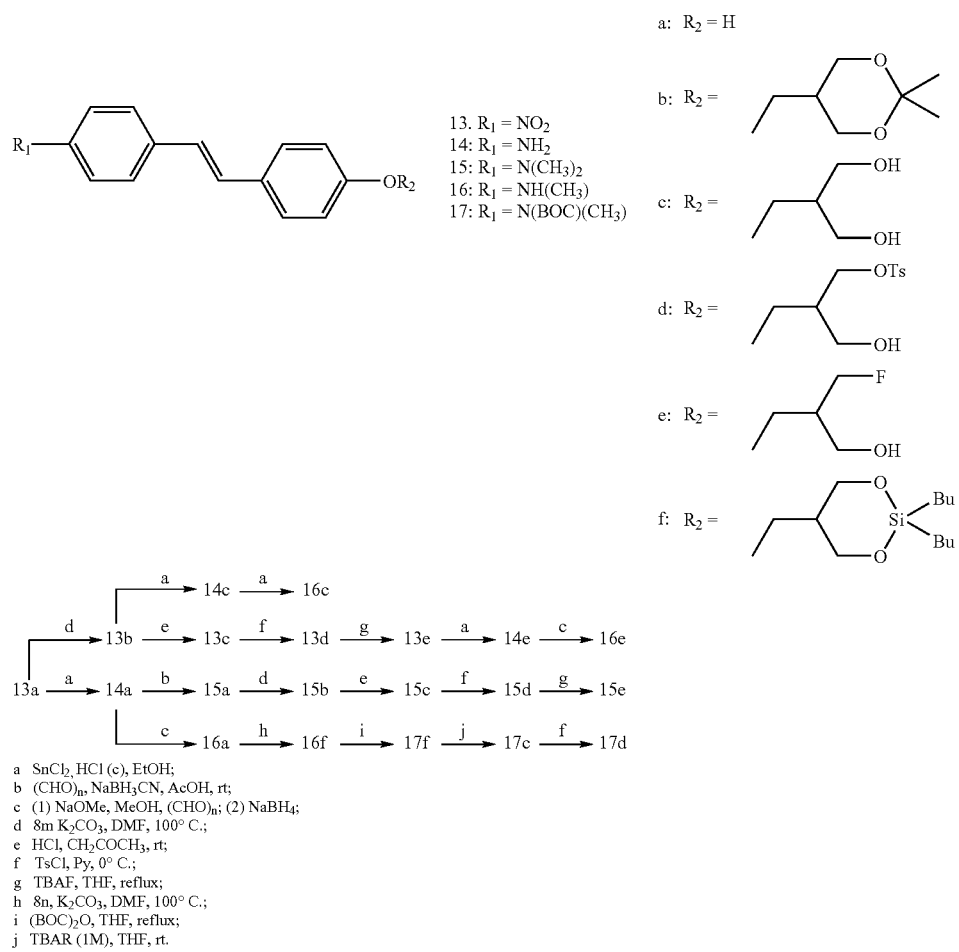
a  SnCl$_2$, HCl (c), EtOH;
b  (CHO)$_n$, NaBH$_3$CN, AcOH, rt;
c  (1) NaOMe, MeOH, (CHO)$_n$; (2) NaBH$_4$;
d  8m K$_2$CO$_3$, DMF, 100° C.;
e  HCl, CH$_2$COCH$_3$, rt;
f  TsCl, Py, 0° C.;
g  TBAF, THF, reflux;
h  8n, K$_2$CO$_3$, DMF, 100° C.;
i  (BOC)$_2$O, THF, reflux;
j  TBAR (1M), THF, rt.
SCHEME 5
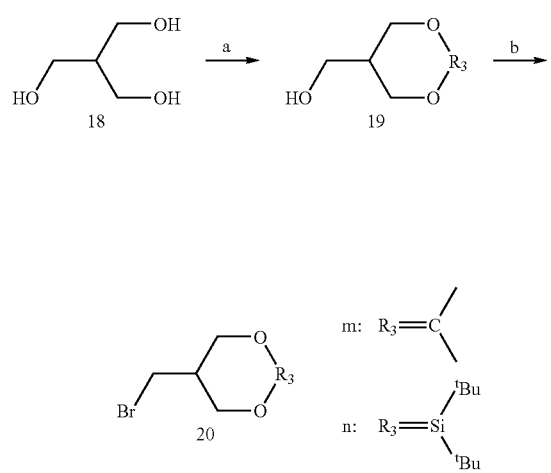
a  7m(CH$_3$O)$_2$C(CH$_3$)$_2$, T$_s$OH; 7n: HOBT, Si(t-BU)$_2$Cl$_2$, Et3N, DCM;
b  CBr$_4$, PPh$_3$, Py, DCM
SCHEME 6
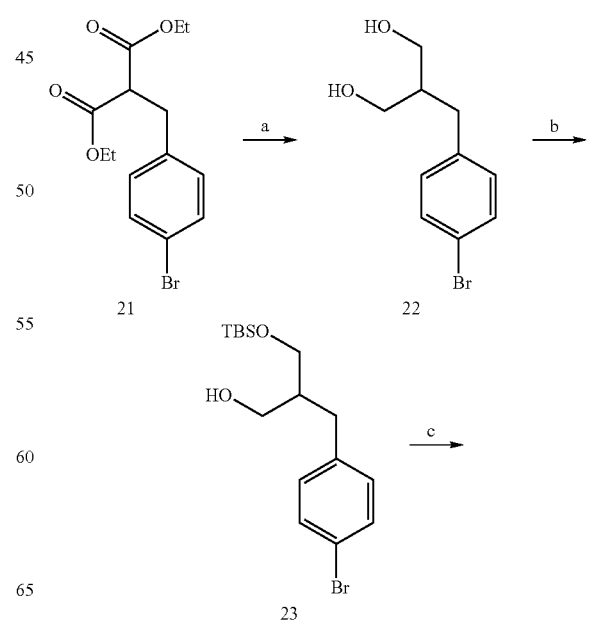

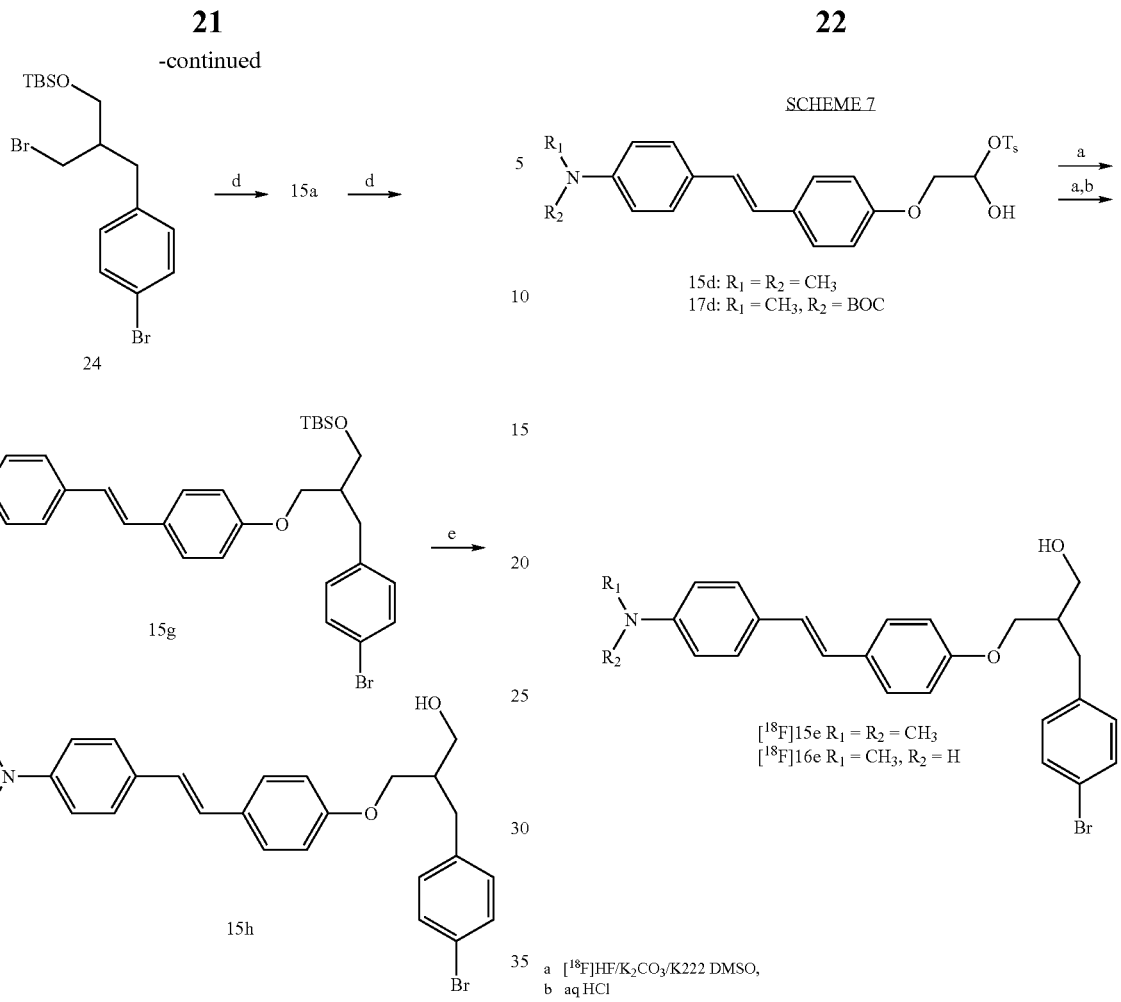
SCHEME 7
a [18F]HF/K2CO3/K222 DMSO,
b aq HCl
SCHEME 8
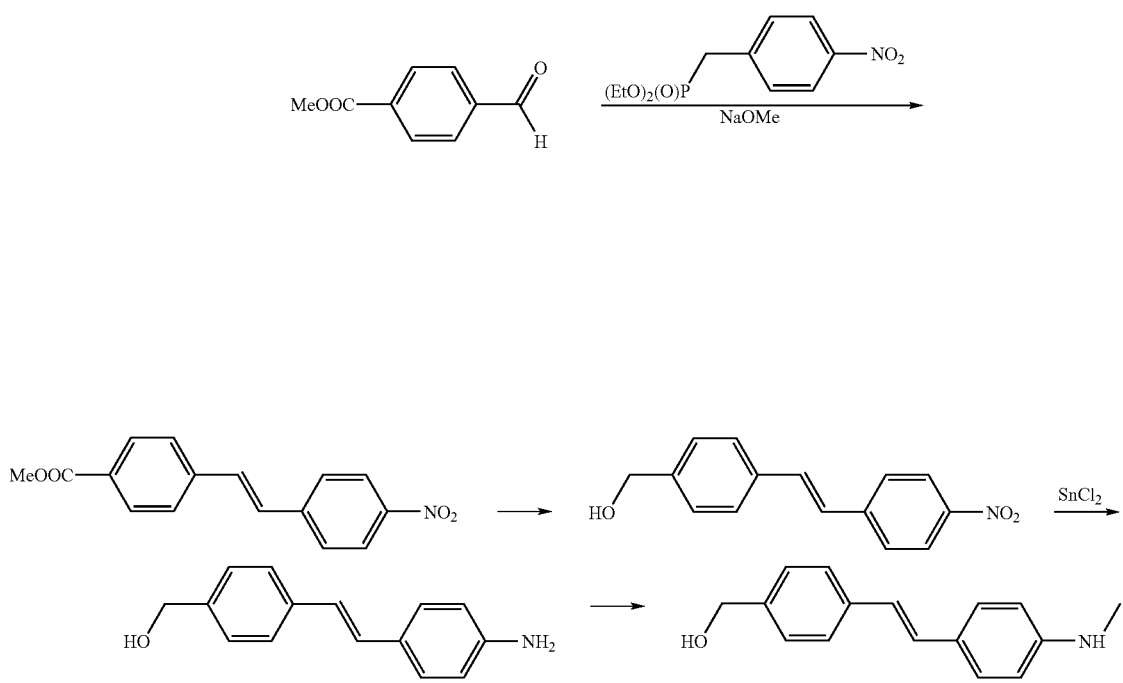

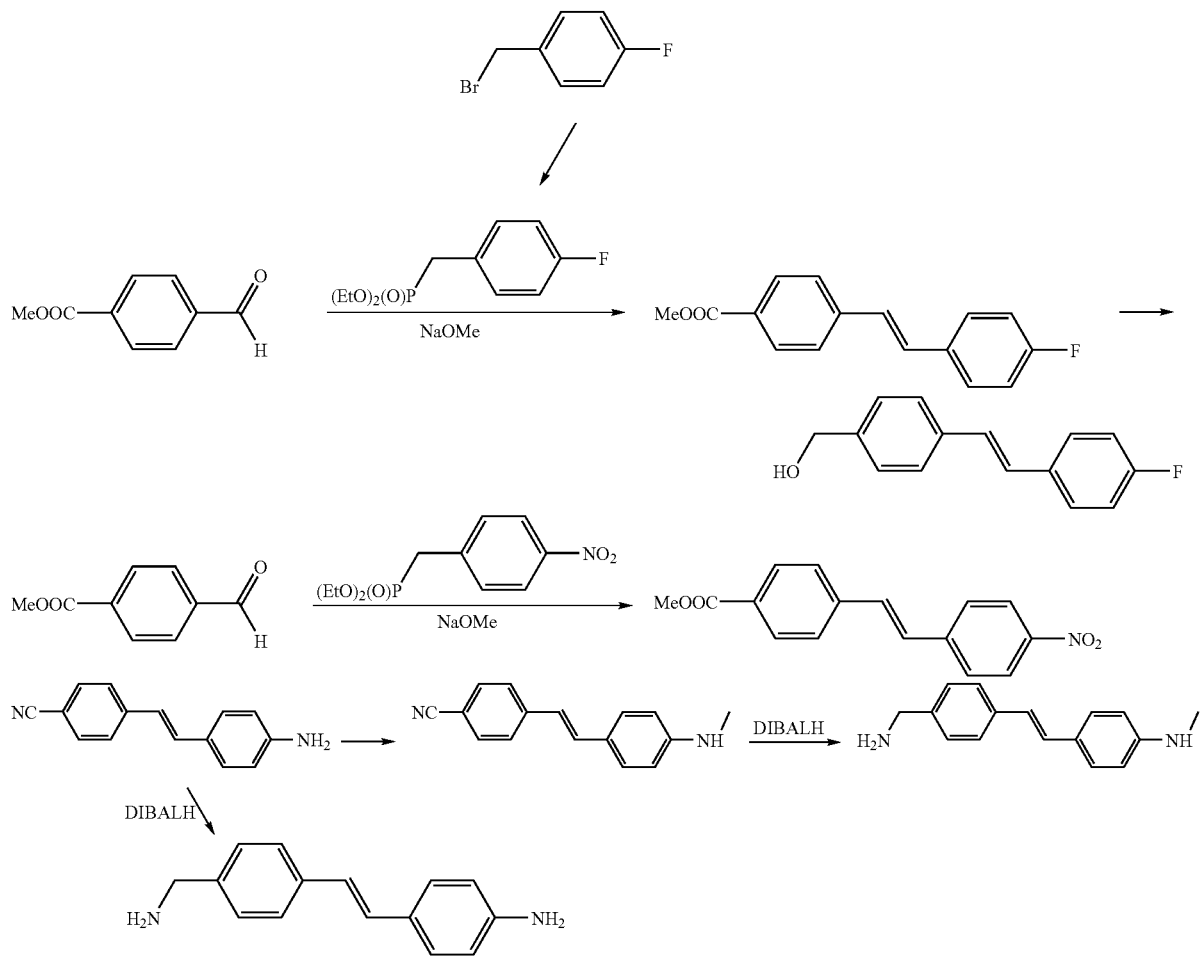

Some of the compounds are also amenable to microwave synthesis as described below in Examples 50-52.

The radiohalogenated compounds of this invention lend themselves easily to formation from materials which could be provided to users in kits. Kits for forming the imaging agents can contain, for example, a vial containing a physiologically suitable solution of an intermediate of Formula I, in a concentration and at a pH suitable for optimal complexing conditions. The user would add to the vial an appropriate quantity of the radioisotope, and an oxidant, such as hydrogen peroxide. The resulting labeled ligand may then be administered intravenously to a patient, and receptors in the brain imaged by means of measuring the gamma ray or photo emissions therefrom.

When desired, the radioactive diagnostic agent may contain any additive such as pH controlling agents (e.g., acids, bases, buffers), stabilizers (e.g., ascorbic acid) or isotonizing agents (e.g., sodium chloride).

The term "pharmaceutically acceptable salt" as used herein refers to those carboxylate salts or acid addition salts of the compounds of the present invention which are, within the scope of sound medical judgement, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively nontoxic, inorganic and organic acid addition salts of compounds of the present invention. Also included are those salts derived from non-toxic organic acids such as aliphatic mono and dicarboxylic acids, for example acetic acid, phenyl-substituted alkanoic acids, hydroxy alkanoic and alkanedioic acids, aromatic acids, and aliphatic and aromatic sulfonic acids. These salts can be prepared in situ during the final isolation and purification of the compounds or by separately reacting the purified compound in its free base form with a suitable organic or inorganic acid and isolating the salt thus formed. Further representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactiobionate and laurylsulphonate salts, propionate, pivalate, cyclamate, isethionate, and the like. These may include cations based on the alkali and alkaline earth metals, such as sodium, lithium, potassium, calcium, magnesium, and the like, as well as, nontoxic ammonium, quaternary ammonium and amine cations including, but not limited to ammonium, tetramethylammonium, tetraethylammonium, methylamine, dimethylamine, trimethylamine, triethylamine, ethylamine, and the like. (See, for example, Berge S.

M., et al., *Pharmaceutical Salts*, *J. Pharm. Sci.* 66:1-19 (1977) which is incorporated herein by reference.)

The present invention is also directed at a method of imaging amyloid deposits. One of the key prerequisites for an in vivo imaging agent of the brain is the ability to cross the intact blood-brain barrier after a bolus iv injection.

In the first step of the present method of imaging, a labeled compound of Formula I, II or III is introduced into a tissue or a patient in a detectable quantity. The compound is typically part of a pharmaceutical composition and is administered to the tissue or the patient by methods well known to those skilled in the art.

For example, the compound can be administered either orally, rectally, parenterally (intravenous, by intramuscularly or subcutaneously), intracisternally, intravaginally, intraperitoneally, intravesically, locally (powders, ointments or drops), or as a buccal or nasal spray.

In a preferred embodiment of the invention, the labeled compound is introduced into a patient in a detectable quantity and after sufficient time has passed for the compound to become associated with amyloid deposits, the labeled compound is detected noninvasively inside the patient. In another embodiment of the invention, an $^{18}F$ labeled compound of Formula I, II or III is introduced into a patient, sufficient time is allowed for the compound to become associated with amyloid deposits, and then a sample of tissue from the patient is removed and the labeled compound in the tissue is detected apart from the patient. In a third embodiment of the invention, a tissue sample is removed from a patient and a labeled compound of Formula I, II or III is introduced into the tissue sample. After a sufficient amount of time for the compound to become bound to amyloid deposits, the compound is detected.

The administration of the labeled compound to a patient can be by a general or local administration route. For example, the labeled compound may be administered to the patient such that it is delivered throughout the body. Alternatively, the labeled compound can be administered to a specific organ or tissue of interest. For example, it is desirable to locate and quantitate amyloid deposits in the brain in order to diagnose or track the progress of Alzheimer's disease in a patient.

The term "tissue" means a part of a patient's body. Examples of tissues include the brain, heart, liver, blood vessels, and arteries. A detectable quantity is a quantity of labeled compound necessary to be detected by the detection method chosen. The amount of a labeled compound to be introduced into a patient in order to provide for detection can readily be determined by those skilled in the art. For example, increasing amounts of the labeled compound can be given to a patient until the compound is detected by the detection method of choice. A label is introduced into the compounds to provide for detection of the compounds.

The term "patient" means humans and other animals. Those skilled in the art are also familiar with determining the amount of time sufficient for a compound to become associated with amyloid deposits. The amount of time necessary can easily be determined by introducing a detectable amount of a labeled compound of Formula I, II or III into a patient and then detecting the labeled compound at various times after administration.

The term "associated" means a chemical interaction between the labeled compound and the amyloid deposit. Examples of associations include covalent bonds, ionic bonds, hydrophilic-hydrophilic interactions, hydrophobic-hydrophobic interactions, and complexes.

Those skilled in the art are familiar with positron emission tomography (PET) detection of a positron-emitting atom, such as $^{18}F$. The present invention is also directed to specific compounds where the $^{18}F$ atom is replaced with a non-radiolabeled fluorine atom.

The radioactive diagnostic agent should have sufficient radioactivity and radioactivity concentration which can assure reliable diagnosis. The desired level of radioactivity can be attained by the methods provided herein for preparing compounds of Formula I, II or III.

The imaging of amyloid deposits can also be carried out quantitatively so that the amount of amyloid deposits can be determined.

Another aspect of the invention is a method of inhibiting amyloid plaque aggregation. The present invention also provides a method of inhibiting the aggregation of amyloid proteins to form amyloid deposits, by administering to a patient an amyloid inhibiting amount of a compound of the above Formula I, II or III.

Those skilled in the art are readily able to determine an amyloid inhibiting amount by simply administering a compound of Formula I, II or II to a patient in increasing amounts until the growth of amyloid deposits is decreased or stopped. The rate of growth can be assessed using imaging as described above or by taking a tissue sample from a patient and observing the amyloid deposits therein. The compounds of the present invention can be administered to a patient at dosage levels in the range of about 0.1 to about 1,000 mg per day. For a normal human adult having a body weight of about 70 kg, a dosage in the range of about 0.01 to about 100 mg per kilogram of body weight per day is sufficient. The specific dosage used, however, can vary. For example, the dosage can depend on a number of factors including the requirements of the patient, the severity of the condition being treated, and the pharmacological activity of the compound being used. The determination of optimum dosages for a particular patient is well known to those skilled in the art.

The radioactive diagnostic agent should have sufficient radioactivity and radioactivity concentration which can assure reliable diagnosis. The desired level of radioactivity can be attained by the methods provided herein for preparing compounds of Formula I, II or III.

The imaging of amyloid deposits can also be carried out quantitatively so that the amount of amyloid deposits can be determined.

The following examples are illustrative, but not limiting, of the method and compositions of the present invention. Other suitable modifications and adaptations of the variety of conditions and parameters normally encountered and obvious to those skilled in the art are within the spirit and scope of the invention.

All reagents used in synthesis were commercial products and were used without further purification unless otherwise indicated. $^1H$ NMR spectra were obtained on a Bruker DPX spectrometer (200 MHz) in $CDCl_3$. Chemical shifts are reported as δ values (parts per million) relative to internal TMS. Coupling constants are reported in hertz. The multiplicity is defined by s (singlet), d (doublet), t (triplet), br (broad), m (multiplet). Elemental analyses were performed by Atlantic Microlab INC. For each procedure, "standard workup" refers to the following steps: addition of indicated organic solvent, washing the organic layer with water then brine, separation of the organic layer from the aqueous layer, drying off the combined the organic layers with anhydrous sodium sulfate, filtering off the sodium sulfate and removing the organic solvent under reduced pressure.

EXAMPLE 1

2-(2-{4-[2-(4-Methylamino-phenyl)-vinyl]-phenoxy}-ethoxy)-ethanol (3a)

Under the nitrogen atmosphere, 4-methylamino-4'-hydroxy stilbene, 1 (Ono M, et al., *Nucl Med Biol.* 2003; Wilson A, et al., *J Labelled Cpd Radiopharm.* 2003) (63 mg, 0.28 mmol) and 2a (42 mg, 0.34 mmol) were dissolved in anhydrous DMF (5.0 ml) followed by an addition of potassium carbonate (125 mg, 0.91 mmol). The suspension was heated to 100° C. and stirred overnight. After cooled down to room temperature, standard workup with dichloromethane was applied and the residue was purified by silica gel preparative TLC (4% methanol in dichloromethane) to afford compound 3a (67 mg, 76%): $^1$H NMR δ 7.37 (m, 4H), 6.89 (m, 4H), 6.63 (d, 2H, J=8.48 Hz), 4.16 (t, 2H), 3.88 (t, 2H), 3.78 (t, 2H), 3.68 (t, 2H), 2.87 (s, 3H), 2.20 (br, 1H), 1.55 (br, 1H).

EXAMPLE 2

2-[-2-(2-{4-[2-(4-Methylamino-phenyl)-vinyl]-phenoxy}-ethoxy)-ethoxy]-ethanol (3b)

Compound 3b was prepared from 1 (150 mg, 0.67 mmol), 2b (136 mg, 0.81 mmol), and potassium carbonate (277 mg, 2.01 mmol) in DMF (10 ml) with the same procedure described for compound 3a. 3b (180 mg, 76%): $^1$H NMR δ 7.37 (m, 4H), 6.89 (m, 4H), 6.65 (d, 2H, J=8.50 Hz), 4.15 (t, 2H), 3.87 (t, 2H), 3.72 (t, 6H), 3.62 (t, 2H), 2.87 (s, 3H), 2.20 (br, 1H), 1.60 (b, 1H).

EXAMPLE 3

2-{2-[2-(2-{4-[2-(4-Methylamino-phenyl)-vinyl]-phenoxy}-ethoxy)-ethoxy]-ethoxy}-ethanol (3c)

TBAF (1 M in THF, 0.06 ml) was added via a syringe to a solution of compound 7c (12 mg, 0.023 mmol) in THF (1 ml). The solution was stirred at room temperature for 2 hours. After standard workup with dichloromethane, the residue was purified by silica gel preparative TLC (4.5% methanol in dichloromethane) to afford 3c (8.7 mg, 94%): 1H NMR δ 7.36 (m, 4H), 6.88 (m, 4H), 6.58 (d, 2H, J=8.5 Hz), 4.15 (t, 2H), 3.86 (t, 2H), 3.70 (m, 12H), 2.86 (s, 3H).

EXAMPLE 4

2-(2-{2-[2-(2-{4-[2-(4-Methylamino-phenyl)-vinyl]-phenoxy}-ethoxy)-ethoxy]-ethoxy}-ethoxy)-ethanol (3d)

Compound 3d was prepared from 7d (15 mg, 0.027 mmol) and TBAF (1 M in THF, 0.06 ml) in THF (1 ml), with the same procedure described for compound 3c. 3d (7.8 mg, 65%): $^1$H NMR δ 7.36 (m, 4H), 6.87 (m, 4H), 6.60 (d, 2H, J=8.5 Hz), 4.14 (t, 2H), 3.85 (t, 2H), 3.66 (m, 16H), 2.86 (s, 3H).

EXAMPLE 5

2-(2-{2-[2-(tert-Butyl-dimethyl-silanyloxy)-ethoxy]-ethoxy}-ethoxy)-ethanol (5c)

Tetraethylene glycol, 4c (1.12 g, 5.77 mmol) and TBDM-SCl (0.87 g, 5.77 mmol) were dissolved in dichloromethane (25 ml) followed by triethyl amine (1.46 g, 14.4 mmol). The solution was stirred at room temperature for 2 hours. After standard workup with dichloromethane, the residue was purified by silica gel column chromatography (50% ethyl acetate in hexane) to afford 5c (744 mg, 42%): $^1$H NMR δ 3.66 (m, 16H), 2.51 (t, 1H, J=5.86 Hz), 0.89 (s, 9H), 0.07 (s, 6H).

EXAMPLE 6

2-[2-(2-{2-[2-(tert-Butyl-dimethyl-silanyloxy)-ethoxy]-ethoxy}-ethoxy)-ethoxy]-ethanol (5d)

Compound 5d was prepared from pentaethylene glycol, 4d (1.13 g, 4.72 mmol), TBDMSCl (0.78 g, 5.19 mmol), and triethyl amine (1.2 g, 11.8 mmol) in dichloromethane (25 ml) with the same procedure described for compound 5c. 5d (668 mg, 40%): $^1$H NMR δ 3.67 (m, 20H), 2.64 (t, 1H, J=5.63 Hz), 0.89 (s, 9H), 0.06 (s, 6H).

EXAMPLE 7

(2-{2-[2-(2-Bromo-ethoxy)-ethoxy]-ethoxy}-ethoxy)-tert-butyl-dimethyl-silane (6c)

Compound 5c (680 mg, 2.20 mmol) and carbon tetrabromide (947 mg, 2.86 mg) were dissolved in dichloromethane (20 ml). The solution was cooled down to 0° C. with an ice bath and pyridine (2.0 ml) was added followed by triphenylphosphine (749 mg, 0.286 mmol). The solution was stirred at 0° C. for half an hour and at room temperature for 2 hours. After standard workup with dichloromethane, the residue was purified by silica gel column chromatography (20% ethyl acetate in hexane) to afford compound 6c (680 mg, 79.6%): $^1$H NMR δ 3.79 (m, 4H), 3.66 (m, 8H), 3.56 (t, 2H), 3.47 (t, 2H), 0.89 (s, 9H), 0.07 (s, 6H).

EXAMPLE 8

[2-(2-{2-[2-(2-Bromoethoxy)-ethoxy]-ethoxy}-ethoxy)-ethoxy]-tert-butyl-dimethylsilane (6d)

Compound 6d was prepared from 5d (624 mg, 1.77 mmol), carbon tetrabromide (761 mg, 2.30 mmol), triphenylphosphine (602 mg, 2.30 mmol), pyridine (2.0 ml) in dichloromethane (20 ml) with the same procedure described for compound 6c. 6d (400 mg, 52.3%): $^1$H NMR δ 3.79 (m, 4H), 3.66 (m, 12H), 3.55 (t, 2H), 3.47 (t, 2H), 0.89 (s, 9H), 0.06 (s, 6H).

EXAMPLE 9

{4-[2-(4-{2-[2-(tert-Butyl-dimethyl-silanyloxy)-ethoxy]-ethoxy}-phenyl)-vinyl]-phenyl}-methyl-amine (7a)

Compound 3a (45 mg, 0.14 mmol) and TBDMSCl (33 mg, 0.22 mmol) were dissolved in dichloromethane (10 ml) followed by imidazole (20 mg, 0.29 mmol). The solution was stirred at room temperature for 2 hours. After standard workup with dichloromethane, the residue was purified by silica gel column chromatography (1.5% methanol in dichloromethane) to afford 7a (56 mg, 91%): $^1$H NMR δ 7.40 (m, 4H), 6.90 (m, 4H), 6.75 (d, 2H, J=7.9 Hz), 4.15 (t, 2H), 3.88 (t, 2H), 3.82 (t, 2H), 3.66 (t, 2H), 2.85 (s, 3H), 0.92 (s, 9H), 0.09 (s, 6H).

EXAMPLE 10

(4-{2-[4-(2-{2-[2-(tert-Butyl-dimethyl-silanyloxy)-ethoxy]-ethoxy}-ethoxy)-phenyl]-vinyl}-phenyl)-methyl-amine (7b)

Compound 7b was prepared from 3b (136 mg, 0.38 mmol), TBDMSCl (86 mg, 0.57 mmol), imidazole (52 mg, 0.76 mmol) in dichloromethane (10 ml) with the same procedure described for compound 7a. 7b (170 mg, 95%): $^1$H NMR δ 7.37 (m, 4H), 6.88 (m, 4H), 6.66 (d, 2H, J=8.6 Hz), 4.14 (t, 2H), 3.86 (t, 2H), 3.75 (m, 6H), 3.57 (t, 2H), 2.88 (s, 3H), 0.90 (s, 9H), 0.07 (s, 6H).

EXAMPLE 11

[4-(2-{4-[2-(2-{2-[2-(tert-Butyl-dimethyl-silanyloxy)-ethoxy]-ethoxy}-ethoxy)-ethoxy]-phenyl}-vinyl)-phenyl]-methyl-amine (7c)

Compound 7c was prepared from 1 (98 mg, 0.44 mmol), 6c (210 mg, 0.57 mmol), K$_2$CO$_3$ (300 mg, 2.18 mmol) in DMF (10 ml), with the same procedure described for compound 3a. 7c (213 mg, 95%): $^1$H NMR δ 7.36 (m, 4H), 6.87 (m, 4H), 6.59 (d, 2H, J=8.5 Hz), 4.14 (t, 2H), 3.86 (t, 2H), 3.75 (m, 10H), 3.55 (t, 2H), 2.86 (s, 3H), 0.89 (s, 9H), 0.06 (s, 6H).

EXAMPLE 12

{4-[2-(4-{2-[2-(2-{2-[2-(tert-Butyl-dimethyl-silanyloxy)-ethoxy]-ethoxy}-ethoxy)-ethoxy]-ethoxy}-phenyl)-vinyl]-phenyl}-methyl-amine (7d)

Compound 7d was prepared from 1 (97 mg, 0.43 mmol), 6d (197 mg, 0.47 mmol), K$_2$CO$_3$ (297 mg, 2.15 mmol) in DMF (10 ml), with the same procedure described for compound 3a. 7d (220 mg, 91%): $^1$H NMR δ 7.36 (m, 4H), 6.87 (m, 4H), 6.59 (d, 2H, J=8.5 Hz), 4.14 (t, 2H), 3.85 (t, 2H), 3.75 (m, 14H), 3.55 (t, 2H), 2.86 (s, 3H), 0.89 (s, 9H), 0.06 (s, 6H).

EXAMPLE 13

{4-[2-(4-{2-[2-(tert-Butyl-dimethyl-silanyloxy)-ethoxy]-ethoxy}-phenyl)-vinyl]-phenyl}-methyl-carbamic acid tert-butyl ester (8a)

Under the nitrogen atmosphere, 7a (54 mg, 0.13 mmol) was dissolved in anhydrous THF (5.0 ml) followed by Boc-anhydride (84 mg, 0.25 mmol). The solution was refluxed overnight. After standard workup with dichloromethane, the residue was purified by silica gel preparative TLC (2% methanol in dichloromethane) to afford 8a (60 mg, 90%): $^1$H NMR δ 7.43 (d, 4H, J=8.4 Hz), 7.20 (d, 2H, J=8.4 Hz), 6.97 (q, 2H), 6.90 (d, 2H, J=8.7 Hz), 4.14 (t, 2H), 3.87 (t, 2H), 3.80 (t, 2H), 3.64 (t, 2H), 3.27 (s, 3H), 1.46 (s, 9H), 0.90 (s, 9H), 0.08 (s, 6H).

EXAMPLE 14

(4-{2-[4-(2-{2-[2-(tert-Butyl-dimethyl-silanyloxy)-ethoxy]-ethoxy}-ethoxy)-phenyl]-vinyl}-phenyl)-methyl-carbamic acid tert-butyl ester (8b)

Compound 8b was prepared from 7b (124 mg, 0.26 mmol) and Boc-anhydride (218 mg, 0.66 mmol) in THF (10 ml), with the same procedure described for compound 8a. 8b (130 mg, 86%): $^1$H NMR δ 7.43 (d, 4H, J=8.4 Hz), 7.20 (d, 2H, J=8.4 Hz), 6.97 (q, 2H), 6.90 (d, 2H, J=8.7 Hz), 4.15 (t, 2H), 3.87 (t, 2H), 3.75 (t, 6H), 3.57 (t, 2H), 3.27 (s, 3H), 1.46 (s, 9H), 0.90 (s, 9H), 0.07 (s, 6H).

EXAMPLE 15

[4-(2-{4-[2-(2-{2-[2-(tert-Butyl-dimethyl-silanyloxy)-ethoxy]-ethoxy}-ethoxy)-ethoxy]-phenyl}-vinyl)-phenyl]-methyl-carbamic acid tert-butyl ester (8c)

Compound 8c was prepared from 7c (84 mg, 0.16 mmol) and Boc-anhydride (163 mg, 0.49 mmol) in THF (5 ml), with the same procedure described for compound 8a. 8c (86 mg, 86%): $^1$H NMR δ 7.42 (d, 4H, J=7.6 Hz), 7.20 (d, 2H, J=8.4 Hz), 6.97 (q, 2H), 6.90 (d, 2H, J=8.7 Hz), 4.15 (t, 2H), 3.87 (t, 2H), 3.73 (t, 10H), 3.57 (t, 2H), 3.26 (s, 3H), 1.46 (s, 9H), 0.89 (s, 9H), 0.07 (s, 6H).

EXAMPLE 16

{4-[2-(4-{2-[2-(2-{2-[2-(tert-Butyl-dimethyl-silanyloxy)-ethoxy]-ethoxy}-ethoxy)-ethoxy]-ethoxy}-phenyl)-vinyl]-phenyl}-methyl-carbamic acid tert-butyl ester (8d)

Compound 8d was prepared from 7d (210 mg, 0.51 mmol) and Boc-anhydride (840 mg, 2.54 mmol) in THF (10 ml), with the same procedure described for compound 8a. 8d (174 mg, 66.7%): $^1$H NMR δ 7.42 (d, 4H, J=8.4 Hz), 7.20 (d, 2H, J=8.4 Hz), 6.97 (q, 2H), 6.90 (d, 2H, J=8.7 Hz), 4.15 (t, 2H), 3.86 (t, 2H), 3.72 (t, 14H), 3.55 (t, 2H), 3.27 (s, 3H), 1.46 (s, 9H), 0.89 (s, 9H), 0.06 (s, 6H).

EXAMPLE 17

[4-(2-{4-[2-(2-Hydroxy-ethoxy)-ethoxy]-phenyl}-vinyl)-phenyl]-methyl-carbamic acid tert-butyl ester (9a)

Compound 9a was prepared from 8a (56 mg, 0.11 mmol) and TBAF (1 M in THF, 0.21 ml) in THF (5 ml), with the same procedure described for compound 3c. 9a (36 mg, 82%): $^1$H NMR δ 7.43 (d, 4H, J=8.4 Hz), 7.20 (d, 2H, J=8.4 Hz), 6.97 (q, 2H), 6.90 (d, 2H, J=8.7 Hz), 4.18 (t, 2H), 3.88 (t, 2H), 3.78 (t, 2H), 3.68 (t, 2H), 3.27 (s, 3H), 1.46 (s, 9H).

EXAMPLE 18

{4-[2-(4-{2-[2-(2-Hydroxy-ethoxy)-ethoxy]-ethoxy}-phenyl)-vinyl]-phenyl}-methyl-carbamic acid tert-butyl ester (9b)

Compound 9b was prepared from 8b (118 mg, 0.21 mmol) and TBAF (1 M in THF, 0.42 ml) in THF (10 ml), with the same procedure described for compound 3c. 9b (94 mg, 99.7%): $^1$H NMR δ 7.43 (d, 4H, J=8.4 Hz), 7.20 (d, 2H, J=8.4 Hz), 6.97 (q, 2H), 6.90 (d, 2H, J=8.7 Hz), 4.17 (t, 2H), 3.87 (t, 2H), 3.74 (t, 6H), 3.62 (t, 2H), 3.27 (s, 3H), 1.46 (s, 9H).

EXAMPLE 19

(4-{2-[4-(2-{2-[2-(2-Hydroxy-ethoxy)-ethoxy]-ethoxy}-ethoxy)-phenyl]-vinyl}-phenyl)-methyl-carbamic acid tert-butyl ester (9c)

Compound 9c was prepared from 8b (66 mg, 0.11 mmol), TBAF (1 M in THF, 0.22 ml) and THF (5 ml), with the same procedure described for compound 3c. 9c (50 mg, 93.0%): $^1$H NMR δ 7.43 (d, 4H, J=8.4 Hz), 7.20 (d, 2H, J=8.4 Hz), 6.97 (q, 2H), 6.90 (d, 2H, J=8.7 Hz), 4.16 (t, 2H), 3.87 (t, 2H), 3.78 (t, 10H), 3.61 (t, 2H), 3.27 (s, 3H), 1.46 (s, 9H).

EXAMPLE 20

[4-(2-{4-[2-(2-{2-[2-(2-Hydroxy-ethoxy)-ethoxy]-ethoxy}-ethoxy)-ethoxy]-phenyl}-vinyl)-phenyl]-methyl-carbamic acid tert-butyl ester (9d)

Compound 9d was prepared from 8d (76 mg, 0.12 mmol) and TBAF (1 M in THF, 0.24 ml) in THF (5 ml), with the same procedure described for compound 3c. 9d (52 mg, 82.7%): $^1$H NMR δ 7.43 (d, 4H, J=8.4 Hz), 7.20 (d, 2H, J=8.4 Hz), 6.97 (q, 2H), 6.90 (d, 2H, J=8.7 Hz), 4.16 (t, 2H), 3.87 (t, 2H), 3.75 (t, 14H), 3.60 (t, 2H), 3.27 (s, 3H), 1.46 (s, 9H).

EXAMPLE 21

Methanesulfonic acid 2-[2-(4-{2-[4-(tert-butoxycarbonyl-methyl-amino)-phenyl]-vinyl}-phenoxy)-ethoxy]-ethyl ester(10a)

Compound 9a (36 mg, 0.087 mmol) was dissolved in dichloromethane (5 ml) followed by triethylamine (44 mg, 0.44 mmol). Methanesulfonyl chloride (30 mg, 0.26 mmol) was then added via a syringe. The solution was stirred at room temperature for 4 hours. After standard workup with dichloromethane, the residue was purified by silica gel preparative TLC (2.0% methanol in dichloromethane) to afford 10a (39 mg, 91%): $^1$H NMR δ 7.43 (d, 4H, J=8.6 Hz), 7.20 (d, 2H, J=8.4 Hz), 6.98 (q, 2H), 6.89 (d, 2H, J=8.6 Hz), 4.41 (m, 2H), 4.16 (m, 2H), 3.87 (m, 4H), 3.27 (s, 3H), 3.05 (s, 3H), 1.46 (s, 9H). Anal. ($C_{25}H_{33}NO_7S$)C. H. N.

EXAMPLE 22

Methanesulfonic acid 2-{2-[2-(4-{2-[4-(tert-butoxycarbonyl-methyl-amino)-phenyl]-vinyl}-phenoxy)-ethoxy]-ethoxy}-ethyl ester (10b)

Compound 10b was prepared from 9b (81 mg, 0.18 mmol), methanesulfonyl chloride (62 mg, 0.54 mmol) and triethylamine (88 mg, 0.88 mmol) in dichloromethane (8 ml), with the same procedure described for compound 10a. 10b (82 mg, 86.5%): $^1$H NMR δ 7.43 (d, 4H, J=8.6 Hz), 7.20 (d, 2H, J=8.4 Hz), 6.97 (q, 2H), 6.90 (d, 2H, J=8.6 Hz), 4.38 (m, 2H), 4.15 (m, 2H), 3.85 (m, 2H), 3.76 (m, 6H), 3.27 (s, 3H), 3.05 (s, 3H), 1.46 (s, 9H). Anal. ($C_{27}H_{37}NO_8S$)C. H. N.

EXAMPLE 23

Methanesulfonic acid 2-(2-{2-[2-(4-{2-[4-(tert-butoxycarbonyl-methyl-amino)-phenyl]-vinyl}-phenoxy)-ethoxy]-ethoxy}-ethoxy)-ethyl ester (10c)

Compound 10c was prepared from 9c (50 mg, 0.10 mmol), methanesulfonyl chloride (46 mg, 0.40 mmol) and triethylamine (50 mg, 0.50 mmol) in dichloromethane (5 ml), with the same procedure described for compound 10a. 10c (56 mg, 96.9%): $^1$H NMR δ 7.43 (d, 4H, J=8.6 Hz), 7.20 (d, 2H, J=8.4 Hz), 6.97 (q, 2H), 6.90 (d, 2H, J=8.6 Hz), 4.37 (m, 2H), 4.16 (m, 2H), 3.86 (m, 2H), 3.76 (m, 10H), 3.27 (s, 3H), 3.06 (s, 3H), 1.46 (s, 9H). Anal. ($C_{29}H_{41}NO_9S$)C. H. N.

EXAMPLE 24

Methanesulfonic acid 2-[2-(2-{2-[2-(4-{2-[4-(tert-butoxycarbonyl-methyl-amino)-phenyl]-vinyl}-phenoxy)-ethoxy]-ethoxy}-ethoxy]-ethoxy)-ethyl ester (10d)

Compound 10d was prepared from 9d (58 mg, 0.11 mmol), methanesulfonyl chloride (49 mg, 0.43 mmol) and triethylamine (54 mg, 0.54 mmol) in dichloromethane (5 ml), with the same procedure described for compound 10a. 10d (63 mg, 95%): $^1$H NMR δ 7.43 (d, 4H, J=8.6 Hz), 7.20 (d, 2H, J=8.4 Hz), 6.97 (q, 2H), 6.90 (d, 2H, J=8.6 Hz), 4.37 (m, 2H), 4.18 (m, 2H), 3.86 (m, 2H), 3.75 (m, 14H), 3.27 (s, 3H), 3.07 (s, 3H), 1.46 (s, 9H). Anal. ($C_{31}H_{45}NO_{10}S$)C. H. N.

EXAMPLE 25

[4-(2-{4-[2-(2-Fluoro-ethoxy)-ethoxy]-phenyl}-vinyl)-phenyl]-methyl-carbamic acid tert-butyl ester (11a)

Anhydrous TBAF (Cox D P, et al., *J Org Chem.* 1984; 49:3216-19) (38.5 mg 0.15 mmol) was added to a solution of compound 10a (14.5 mg, 0.03 mmol) in anhydrous THF (3 ml). The mixture was refluxed for 4 hours. After cooled to room temperature, standard workup with dichloromethane was applied and the residue was purified by silica gel preparative TLC (2% methanol in dichloromethane) to afford compound 11a (7 mg, 57%): $^1$H NMR δ 7.43 (d, 4H, J=8.6 Hz), 7.20 (d, 2H, J=8.4 Hz), 6.97 (q, 2H), 6.91 (d, 2H, J=8.6 Hz), 4.60 (d, t, 2H, J1=47 Hz, J2=4.0 Hz), 4.17 (t, 2H), 3.90 (t, 3H), 3.75 (t, 1H), 3.27 (s, 3H), 1.46 (s, 9H).

EXAMPLE 26

{4-[2-(4-{2-[2-(2-Fluoro-ethoxy)-ethoxy]-ethoxy}-phenyl)-vinyl]-phenyl}-methyl-carbamic acid tert-butyl ester (11b)

Compound 11b was prepared from 10b (21 mg, 0.04 mmol) and TBAF (52 mg, 0.2 mmol) in THF (10 ml), with the same procedure described for compound 11a. 11b (17 mg, 94%): $^1$H NMR δ 7.43 (d, 4H, J=8.6 Hz), 7.20 (d, 2H, J=8.4 Hz), 6.97 (q, 2H), 6.91 (d, 2H, J=8.6 Hz), 4.58 (d, t, 2H, J1=48 Hz, J2=4.0 Hz), 4.16 (t, 2H), 3.85 (t, 3H), 3.74 (t, 5H), 3.26 (s, 3H), 1.46 (s, 9H).

EXAMPLE 27

(4-{2-[4-(2-{2-[2-(2-Fluoro-ethoxy)-ethoxy]-ethoxy}-ethoxy)-phenyl]-vinyl}-phenyl)-methyl-carbamic acid tert-butyl ester (11c)

Compound 11c was prepared from 10c (18 mg, 0.03 mmol) and TBAF (42 mg, 0.16 mmol) in THF (5 ml), with the same procedure described for compound 11a. 11c (12 mg, 77%): $^1$H NMR δ 7.43 (d, 4H, J=8.6 Hz), 7.20 (d, 2H, J=8.4 Hz), 6.97 (q, 2H), 6.91 (d, 2H, J=8.6 Hz), 4.67 (t, 1H), 4.55 (d, t, 2H, J1=48 Hz, J2=4.0 Hz), 3.85 (t, 3H), 3.74 (t, 9H), 3.27 (s, 3H), 1.46 (s, 9H).

EXAMPLE 28

[4-(2-{4-[2-(2-{2-[2-(2-Fluoro-ethoxy)-ethoxy]-ethoxy}-ethoxy)-ethoxy]-phenyl}-vinyl)-phenyl]-methyl-carbamic acid tert-butyl ester (11d)

Compound 11d was prepared from 10d (15 mg, 0.024 mmol) and TBAF (32 mg, 0.12 mmol) in THF (5.0 ml), with the same procedure described for compound 11a. 11d (11 mg, 84%): $^1$H NMR δ 7.43 (d, 4H, J=8.4 Hz), 7.20 (d, 2H, J=8.4 Hz), 6.97 (q, 2H), 6.90 (d, 2H, J=8.6 Hz), 4.55 (d, t, 2H, J1=48 Hz, J2=4.0 Hz), 4.15 (t, 2H), 3.86 (t, 3H), 3.72 (t, 13H), 3.26 (s, 3H), 1.46 (s, 9H).

EXAMPLE 29

[4-(2-{4-[2-(2-Fluoro-ethoxy)-ethoxy]-phenyl}-vinyl)-phenyl]-methyl-amine (12a)

Trifluoroacetic acid (0.5 ml) was added slowly to a solution of compound 11a (7.0 mg, 0.017 mmol) in dichloromethane (1 ml). The mixture was then stirred at room temperature for 1 hour. After standard workup with dichloromethane, the residue was purified by silica gel preparative TLC (1.0% methanol in dichloromethane) to afford 12a (3 mg, 56%): $^1$H NMR δ 7.37 (m, 4H), 6.90 (m, 4H), 6.65 (d, 2H, J=8.4 Hz), 4.60 (d, t, 2H, J$_1$=46 Hz, J2=4.0 Hz), 4.17 (t, 2H), 3.90 (t, 3H), 3.76 (t, 1H), 2.88 (s, 3H). Anal. ($C_{19}H_{22}FNO_2$)C. H. N.

EXAMPLE 30

{4-[2-(4-{2-[2-(2-Fluoro-ethoxy)-ethoxy]-ethoxy}-phenyl)-vinyl]-phenyl}-methyl-amine (12b)

Compound 12b was prepared from 11b (17 mg, 0.037 mmol) in trifluoroacetic acid (1 ml) and dichloromethane (2 ml), with the same procedure described for compound 12a. 12b (9 mg, 68%): $^1$H NMR δ 7.37 (m, 4H), 6.88 (m, 4H), 6.64 (d, 2H, J=8.4 Hz), 4.56 (d, t, 2H, J1=46 Hz, J2=4.0 Hz), 4.15 (t, 2H), 3.87 (m, 3H), 3.70 (m, 5H), 2.87 (s, 3H). Anal. ($C_{21}H_{26}FNO_3$)C. H. N.

EXAMPLE 31

(4-{2-[4-(2-{2-[2-(2-Fluoro-ethoxy)-ethoxy]-ethoxy}-ethoxy)-phenyl]-vinyl}-phenyl)-methyl-amine (12c)

Compound 12c was prepared from 11e (12 mg, 0.024 mmol) in trifluoroacetic acid (0.5 ml) and dichloromethane (1 ml), with the same procedure described for compound 12a. 12c (7 mg, 73%): $^1$H NMR δ 7.37 (m, 4H), 6.89 (m, 4H), 6.62 (d, 2H, J=8.4 Hz), 4.55 (d, t, 2H, J$_1$=46 Hz, J2=4.0 Hz), 4.15 (t, 2H), 3.86 (m, 3H), 3.71 (m, 9H), 2.87 (s, 3H). Anal. ($C_{23}H_{30}FNO_4$)C. H. N.

EXAMPLE 32

[4-(2-{4-[2-(2-{2-[2-(2-Fluoro-ethoxy)-ethoxy]-ethoxy}-ethoxy)-ethoxy]-phenyl}-vinyl)-phenyl]-methyl-amine (12d)

Compound 12d was prepared from 11d (10 mg, 0.018 mmol) in trifluoroacetic acid (0.3 ml) and dichloromethane (1 ml), with the same procedure described for compound 12a. 12d (6 mg, 73%): $^1$H NMR δ 7.37 (m, 4H), 6.88 (m, 4H), 6.64 (d, 2H, J=8.4 Hz), 4.55 (d, t, 2H, J$_1$=46 Hz, J2=4.0 Hz), 4.14 (t, 2H), 3.87 (m, 3H), 3.70 (m, 13H), 2.87 (s, 3H). Anal. ($C_{25}H_{34}FNO_5$)C. H. N.

EXAMPLE 33

[$^{18}$F][4-(2-{4-[2-(2-Fluoro-ethoxy)-ethoxy]-phenyl}-vinyl)-phenyl]-methyl-amine ([$^{18}$F]12a)

[$^{18}$F]Fluoride, produced by a cyclotron using $^{18}$O(p,n)$^{18}$F reaction, was passed through a Sep-Pak Light QMA cartridge as an aqueous solution in [$^{18}$O]-enriched water. The cartridge was dried by airflow, and the $^{18}$F activity was eluted with 2 mL of Kryptofix 222 (K222)/$K_2CO_3$ solution (22 mg of K222 and 4.6 mg of $K_2CO_3$ in $CH_3CN/H_2O$ 1.77/0.23). The solvent was removed at 120° C. under an argon stream. The residue was azeotropically dried with 1 mL of anhydrous $CH_3CN$ twice at 120° C. under an argon stream. A solution of mesylate precursor 10a (4 mg) in DMSO (0.2 mL) was added to the reaction vessel containing the dried $^{18}$F activities. The solution was heated at 120° C. for 4 min. Water (2 mL) was added and the solution was cooled down for 1 min. HCl (10% aq solution, 0.5 mL) was then added and the mixture was heated at 120° C. again for 5 min. Aqueous solution of NaOH was added to adjust the pH to basic (pH 8-9). The mixture was extracted with ethyl acetate (1 mL×2) and the combined organic layer was dried ($Na_2SO_4$), and the solvent removed under argon stream with gentle heating (55-60° C.). The residue was dissolved in $CH_3CN$ and injected to HPLC for purification. [Hamilton PRP-1 semi-prep column (7.0×305 mm, 10 µm), $CH_3CN$/dimethylglutarate buffer (5 mM, pH 7) 9/1; Flow rate 2 mL/min]. Retention time of 12a was 8.9 min in this HPLC system and well separated from precursor 10a (rt=12 min) as well as the hydrolysis by-product (rt=6.2 min). The preparation took 90 min and the radiochemical yield was 20% (decay corrected). To determine radiochemical purity and specific activity (Spec. Act.), analytical HPLC was used [Hamilton PRP-1 analytical column (4.1×250 mm, 10 µm), $CH_3CN$/dimethylglutarate buffer (5 mM, pH 7) 9/1; Flow rate 0.5 mL/min]. Retention time of 12a in this system was 10.8 min and RCP was over 99%. Specific activity was estimated by comparing UV peak intensity of purified [$^{18}$F]10 with reference non-radioactive compound of known concentration. The specific activity (Spec. Act.) was 1,000-1,500 Ci/mmol after the preparation.

EXAMPLE 34

[$^{18}$F]{4-[2-(4-{2-[2-(2-Fluoro-ethoxy)-ethoxy]-ethoxy}-phenyl)-vinyl]-phenyl}-methyl-amine ([$^{18}$F]12b)

Using a similar reaction [$^{18}$F]12b was obtained from 10b. Radiochemical yield was 30% (decay corrected) and radiochemical purity was >99%. HPLC retention time of 12b was 11.7 min for the analytical system described above (Spec. Act.=1,300-1,500 Ci/mmol).

EXAMPLE 35

[$^{18}$F][(4-{2-[4-(2-{2-[2-(2-Fluoro-ethoxy)-ethoxy]-ethoxy}-ethoxy)-phenyl]-vinyl}-phenyl)-methyl-amine ([$^{18}$F]12c)

Using a similar reaction [$^{18}$F]12c was obtained from 10c. Radiochemical yield was 10% (decay corrected) and radiochemical purity was >99%. HPLC retention time of 12c was 11.7 min for the analytical system described above (Spec. Act.=900 Ci/mmol).

EXAMPLE 36

[$^{18}$F][[4-(2-{4-[2-(2-{2-[2-(2-Fluoro-ethoxy)-ethoxy]-ethoxy}-ethoxy)-ethoxy]-phenyl}-vinyl)-phenyl]-methyl-amine ([$^{18}$F]12d)

Using a similar reaction [$^{18}$F]12d was obtained from 10b. Radiochemical yield was 20% (decay corrected) and radiochemical purity was >99%. HPLC retention time of 12d was 10.7 min for the analytical system described above (Spec. Act.=1,000-1,500 Ci/mmol).

EXAMPLE 37

4-Amino-4'-hydroxyl stilbene (14a)

Stannous chloride (11.8 g, 0.062 mol) was added to a solution of compound 13a (Frinton Lab) (3.0 g, 0.012 mol) in ethanol (100 mL) followed by the addition of concentrated hydrochloric acid (5.0 mL). The solution was brought to reflux for 3 hr and cooled to room temperature stirring overnight. Aqueous sodium hydroxide (1N) was added to adjust the pH to 8.5-9. After standard workup with dichloromethane, crude product 14a was obtained (2.6 g, ~100%). The product was used in following step without further purifications. $^1$H NMR (DMSO-d$_6$) δ 9.39 (s, 1H), 7.30 (d, 2H, J=8.5 Hz), 7.20 (d, 2H, J=8.5 Hz), 6.80 (m, 2H), 6.72 (d, 2H, J=8.5 Hz), 6.53 (d, 2H, J=8.5 Hz), 5.19 (s, 2H).

EXAMPLE 38

4-N,N'-Dimethylamino-4'-hydroxyl stilbene (15a)

To a mixture of 14a (211 mg, 1.0 mmol), paraformaldehyde (300 mg, 10 mmol) and sodium cyanoborohydride (189 mg, 3.0 mmol), acetic acid (10 mL) was added. The whole mixture was stirred at room temperature overnight and then poured into 100 mL of water. Sodium carbonate was added to adjust the pH to 8-9. After standard workup with 5% methanol in dichloromethane, the residue was purified by silica gel column chromatography (2.5% methanol in dichloromethane) to afford 15a as a white solid (214 mg, 89.5%): $^1$H NMR δ 7.37 (m, 4H), 6.87 (s, 2H), 6.75 (m, 4H), 4.68 (s, 1H), 2.98 (s, 6H).

EXAMPLE 39

4-N,N'-Dimethylamino-4'-(2,2-dimethyl-[1,3]dioxane-5-ylmethoxy) stilbene (15b)

Under the nitrogen atmosphere, 15a (100 mg, 0.38 mmol) was dissolved in anhydrous DMF (5.0 mL). Potassium carbonate (140 mg, 1.0 mmol) was added to this solution followed by 5-bromomethyl-2,2-dimethyl-[1,3]dioxane 20 m$^1$ (105 mg, 0.5 mmol). The mixture was heated to 100° C. and stirred overnight. After cooled down to room temperature, standard workup with dichloromethane was applied and the residue was purified by silica gel preparative TLC (1% methanol in dichloromethane) to afford compound 15b (100 mg, 72%): $^1$H NMR δ 7.38 (m, 4H), 6.88 (m, 4H), 6.70 (d, 2H, J=8.7 Hz), 4.08 (m, 4H), 3.87 (m, 2H), 2.96 (s, 6H), 2.13 (m, 1H), 1.46 (s, 3H), 1.42 (s, 3H). Anal. (C$_{23}$H$_{29}$NO$_3$)C, H, N.

EXAMPLE 40

4-N,N'-Dimethylamino-4'-(1,3-dihydroxy-propane-2-ylmethoxy) stilbene (15c)

Compound 15b (180 mg, 0.49 mmol) was suspended in acetone (5.0 mL) and cooled to 0° C. with an ice bath. 1N HCl (5.0 mL, 5.0 mmol) was slowly added over 20 min. The suspension turned clear solution during the addition. The solution was stirred at 0° C. for additional half an hour and then warmed to room temperature in half an hour. Saturated sodium bicarbonate was added to adjust pH to 8.5-9. After standard workup with dichloromethane, the residue was purified by silica gel preparative TLC (5% methanol in dichloromethane) to afford compound 15c as a white solid (140 mg, 87%): $^1$H NMR δ 7.40 (m, 4H), 6.88 (m, 4H), 6.74 (m, 2H), 4.10 (d, 2H, J=5.47 Hz), 3.89 (d, 4H, J=5.28 Hz), 2.98 (s, 6H), 2.22 (m, 1H). Anal. (C$_{20}$H$_{25}$NO$_3$) C. H. N.

EXAMPLE 41

4-N,N'-Dimethylamino-4'-(1-tosyl-3-hydroxy-propane-2-ylmethoxy) stilbene (15d)

Compound 15c (158 mg, 0.49 mmol) was dissolved in anhydrous pyridine (15 mL) and cooled to 0° C. with an ice bath. Tosyl chloride (137 mg, 0.72 mmol) was added and the solution was stirred at 0° C. for 2 hr. After standard workup with dichloromethane, the residue was purified by silica gel preparative TLC (5% methanol in dichloromethane) to afford monotosylate compound, 15d, as a white solid (95 mg, 41%): $^1$H NMR δ 7.75 (d, 2H, J=8.26 Hz), 7.37 (m, 4H), 7.26 (m, 2H), 6.88 (m, 2H), 6.72 (m, 4H), 4.26 (d, 2H, J=5.66 Hz), 3.97 (d, 2H, J=5.96 Hz), 3.79 (d, 2H, J=5.24 Hz), 2.95 (s, 6H), 2.38 (m, 4H). Anal. (C$_{27}$H$_{31}$NO$_5$S)C, H, N.

EXAMPLE 42

4-N,N'-Dimethylamino-4'-(1-fluoro-3-hydroxy-propane-2-ylmethoxy) stilbene (15e)

Compound 15d (40 mg, 0.083 mmol) was dissolved in anhydrous THF (5.0 mL). Under the nitrogen atmosphere, anhydrous TBAF (150 mg, 0.5 mmol) in anhydrous THF (1.0 mL) was slowly added. The solution was then heated to reflux for 3 hr. After cooled down to room temperature, standard workup with dichloromethane was applied and the residue was applied for silica gel preparative TLC (5% methanol in dichloromethane) to afford product 15e (17 mg, 62%): $^1$H NMR δ 7.40 (m, 4H), 6.89 (m, 4H), 6.70 (d, 2H, J=8.82 Hz), 4.67 (d d, 2H, J=47.1 Hz, J$_2$=5.46 Hz), 4.10 (d, 2H, J=5.86 Hz), 3.88 (d, 2H, J=5.24 Hz), 2.97 (s, 6H), 2.40 (m, 1H), 1.76 (s, 1H). Anal. (C$_{20}$H$_{24}$FNO$_2$)C, H, N.

EXAMPLE 43

4-Nitro-4'-(2,2-dimethyl-[1,3]dioxane-5-ylmethoxy) stilbene (13b)

Compound 13b was prepared from 13a (241 mg, 1.0 mmol) with the same procedure described for compound 15b. 13b (260 mg, 70%): $^1$H NMR δ 8.19 (d, 2H, J=8.80 Hz), 7.49 (m, 4H), 7.07 (m, 2H), 6.90 (d, 2H, J=8.80 Hz), 4.12 (m, 4H), 3.89 (d, 2H), 2.10 (m, 1H), 1.48 (s, 3H), 1.43 (s, 3H). Anal. calcd. ($C_{21}H_{23}NO_5$)C, H, N.

EXAMPLE 44

4-Nitro-4'-(1,3-dihydroxy-propane-2-ylmethoxy) stilbene (13c)

Compound 13c was prepared from 13b (260 mg, 0.7 mmol) with the same procedure described for compound 15c. 13c (190 mg, 82%): $^1$H NMR (CD$_3$OD) δ 8.19 (d, 2H, J=8.80 Hz), 7.72 (d, 2H, J=8.80 Hz), 7.55 (d, 2H, J=8.70 Hz), 7.24 (q, 2H), 6.96 (d, 2H, J=8.70 Hz), 4.09 (d, 2H, J=5.78 Hz), 3.74 (d, 4H, J=5.94 Hz), 2.14 (m, 1H). Anal. ($C_{18}H_{19}NO_5$)C, H, N.

EXAMPLE 45

4-Nitro-4'-(1-tosyl-3-hydroxy-propane-2-ylmethoxy) stilbene (13d)

Compound 13d was prepared from 13c (80 mg, 0.24 mmol) with the same procedure described for compound 15d. 13d (66 mg, 56%): $^1$H NMR δ 8.18 (d, 2H, J=8.82 Hz), 7.77 (d, 2H, J=8.32 Hz), 7.58 (d, 2H, J=8.82 Hz), 7.45 (d, 2H, J=8.73 Hz), 7.28 (d, 2H, J=8.18 Hz), 7.09 (q, 2H), 6.81 (d, 2H, J=8.73 Hz), 4.27 (d, 2H, J=5.70 Hz), 4.01 (m, 2H), 3.80 (d, 2H, J=5.61 Hz), 2.40 (m, 4H), 2.02 (s, 1H). Anal. ($C_{25}H_{25}NO_7S$) C, H, N.

EXAMPLE 46

4-Nitro-4'-(1-fluoro-3-hydroxy-propane-2-yl-methoxy) stilbene (13e)

Compound 13e was prepared from 13d (33 mg, 0.069 mmol) with the same procedure described for compound 15e. 13e (20 mg, 88%): $^1$H NMR δ 8.19 (d, 2H, J=8.83 Hz), 7.58 (d, 2H, J=8.84 Hz), 7.48 (d, 2H, J=8.74 Hz), 7.10 (q, 2H), 6.94 (d, 2H, J=8.68 Hz), 4.69 (d d, 2H, J$_1$=47.1 Hz, J$_2$=5.36 Hz), 4.15 (d, 2H, J=5.89 Hz), 3.90 (d, 2H, J=5.43 Hz), 2.43 (m, 1H), 1.74 (s, 1H). Anal. ($C_{18}H_{18}FNO_4$)C, H, N.

EXAMPLE 47

4-Amino-4'-(1-fluoro-3-hydroxy-propane-2-yl-methoxy) stilbene (14e)

Compound 14e was prepared from 13e (37 mg, 0.11 mmol) with the same procedure described for compound 14a. 14e (24 mg, 71%): $^1$H NMR δ 7.35 (m, 4H), 6.90 (m, 4H), 6.66 (d, 2H, J=8.54 Hz), 4.69 (d d, 2H, J$_1$=47.1 Hz, J$_2$=5.46 Hz), 4.12 (d, 2H, J=5.84 Hz), 3.90 (d, 2H, J=5.56 Hz), 3.70 (s, 2H), 2.39 (m, 1H), 1.71 (s, 1H). Anal. ($C_{18}H_{20}FNO_2$)C, H, N.

EXAMPLE 48

4-N-Methyl-amino-4'-(1-fluoro-3-hydroxy-propane-2-ylmethoxy) stilbene (16e)

Under the nitrogen atmosphere, sodium methoxide (22 mg, 0.4 mmol) was added to a suspension of compound 14e (24 mg, 0.08 mmol) in methanol (6 mL) followed by paraformaldehyde (12 mg, 0.4 mmol). The solution was heated to reflux for 2 hr and cooled to 0° C. with an ice bath. Sodium borohydride (15 mg, 0.4 mmol) was added in portions. Reaction mixture was brought to reflux again for 1 hr and poured onto crushed ice. After standard workup with dichloromethane, the residue was applied for silica gel preparative TLC (4.5% methanol in dichloromethane) to afford product 16e (23 mg, 92%): $^1$H NMR δ 7.37 (m, 4H), 6.87 (m, 4H), 6.59 (d, 2H, J=8.56 Hz), 4.69 (d, d, 2H, J$_1$=47.1 Hz, J$_2$=5.44 Hz), 4.12 (d, 2H, J=5.86 Hz), 4.00 (s, 1H), 3.89. (d, 2H, J=5.52 Hz), 2.86 (s, 3H), 2.41 (m, 1H), 1.75 (s, 1H). Anal. ($C_{19}H_{22}FNO_2$)C, H, N.

EXAMPLE 49

4-N-Methyl-amino-4'-hydroxy stilbene (16a)

Compound 16a was prepared from 14a (105 mg, 0.5 mmol) with the same procedure as described for compound 16e. 16a (100 mg, 89%): $^1$H NMR δ 7.34 (m, 4H), 6.86 (s, 2H), 6.79 (d, 2H, J=8.58 Hz), 6.60 (d, 2H, J=8.58 Hz), 2.85 (s, 3H).

EXAMPLE 50

General Microwave Procedure for the Preparation of 12 (n=6, 8) Stilbene

Microwave synthesis: The mixture of 16a, alkylating agent (1 eq.), K$_2$CO$_3$ (3 eq.) in DMF (1 mL/0.05 mmol SB-13) was put in a sealed tube and heated in the microwave oven at the following condition: 180° C., 10 min, high absorption level. Solvent was then removed and PTLC [CH$_2$Cl$_2$-MeOH (97:3) as developing solvent]gave the desired product (Yield: 42-60% depending on the alkylating agent used).

EXAMPLE 51

(4-(2-(4-(2-(2-(2-(2-(2-(2-Fluoro-ethoxy)-ethoxy)-ethoxy)-ethoxy)-ethoxy)-ethoxy)-phenyl)-vinyl)-phenyl)-methyl-amine (12, n=6)

Yield=60%. $^1$H NMR (200 MHz, CDCl$_3$): δ 7.2-7.5 (4H, m), 6.8-7.0 (4H, m), 6.59 (2H, d, J=8.4 Hz), 4.55 (2H, d, t, J=46 Hz, J$_2$=4.0 Hz), 4.14 (2H, t), 3.8-3.9 (3H, m), 3.6-3.8 (17H, m), 2.86 (3H, s). HRMS (EI) m/z calcd. for [$C_{27}H_{38}FNO_6$]$^+$ 491.2683, found 491.2667.

EXAMPLE 52

(4-(2-(4-(2-(2-(2-(2-(2-(2-(2-Fluoro-ethoxy)-ethoxy)-ethoxy)-ethoxy)-ethoxy)-ethoxy)-ethoxy)-phenyl)-vinyl)-phenyl)-methyl-amine (12, n=8)

Yield: 42%. $^1$H NMR (200 MHz, CDCl$_3$): δ 7.3-7.5 (4H, m), 6.8-7.0 (4H, m), 6.73 (2H, d, J=8.2 Hz), 4.55 (2H, d, t, J=46 Hz, J$_2$=4.0 Hz), 4.14 (2H, t), 3.8-3.9 (3H, m), 3.5-3.8 (25H, m), 2.89 (3H, s). HRMS (EI) m/z calcd. for [$C_{31}H_{46}NO_8$]$^+$ 579.3207, found 579.3192.

EXAMPLE 53

Preparation of Brain Tissue Homogenates

Postmortem brain tissues were obtained from AD patients at autopsy, and neuropathological diagnosis was confirmed by current criteria (NIA-Reagan Institute Consensus Group, 1997). Homogenates were then prepared from dissected gray matters from AD patients in phosphate buffered saline (PBS, pH 7.4) at the concentration of approximately 100 mg wet tissue/ml (motor-driven glass homogenizer with setting of 6 for 30 sec). The homogenates were aliquoted into 1 ml-portions and stored at −70° C. for 6-12 month without loss of binding signal.

EXAMPLE 54

Binding Studies

As reported previously, [$^{125}$I]IMPY, with 2,200 Ci/mmol specific activity and greater than 95% radiochemical purity, was prepared using the standard iododestannylation reaction and purified by a simplified C-4 mini column (Kung M-P, et al., *Euro J Nucl Med Mol Imag.* 2004; 31:1136-45). Binding assays were carried out in 12×75 mm borosilicate glass tubes. The reaction mixture contained 50 μl of brain homogenates (20-50 μg), 50 μl of [$^{125}$I]IMPY (0.04-0.06 nM diluted in PBS) and 50 μl of inhibitors (10-5-10-10 M diluted serially in PBS containing 0.1% bovine serum albumin, BSA) in a final volume of 1 ml. Nonspecific binding was defined in the presence of IMPY (600 nM) in the same assay tubes. The mixture was incubated at 37° C. for 2 hr and the bound and the free radioactivity were separated by vacuum filtration through Whatman GF/B filters using a Brandel M-24R cell harvester followed by 2×3 ml washes of PBS at room temperature. Filters containing the bound $^{125}$I ligand were assayed for radioactivity content in a gamma counter (Packard 5000) with 70% counting efficiency. Under the assay conditions, the specifically bound fraction was less than 15% of the total radioactivity. The results of inhibition experiments were subjected to nonlinear regression analysis using EBDA by which Ki values were calculated. The results are given in Table 1.

TABLE 1

|  | $K_i$ ± SEM (nM) |  | $K_i$ ± SEM (nM) X = OH |  | $K_i$ ± SEM (nM) X = F |
|---|---|---|---|---|---|
| IMPY | 1.4 ± 0.4* | 3a, n = 2 | 5.2 ± 0.4 | 12a, n = 2 | 2.9 ± 0.2 |
| SB-13 | 1.2 ± 0.7* | 3b, n = 3 | 2.8 ± 0.2 | 12b, n = 3 | 6.7 ± 0.3 |
| PIB | 2.8 ± 0.5+ | 3c, n = 4 | 4.6 ± 0.2 | 12c, n = 4 | 4.4. ± 0.8 |
| FMAPO | 5.0 ± 1.2+ | 3d, n = 5 | 5.2 ± 0.2 | 12d, n = 5 | 6.0 ± 0.8 |

Each value was obtained from three independent measurements performed on duplicate.

The fluorinated PEG stilbenes (12a-d) showed excellent binding affinities ($K_i$=2.9-6.7 nM); while the corresponding hydroxyl substitute analogs (3a-d) also displayed very high binding affinities ($K_i$=2.8-5.2 nM) (Table 1). The lipophilicity of this series of labeled agents, [$^{18}$F]12a-d, was within an appropriate range (log P value was 2.52, 2.41, 2.05 and 2.28 for n=2-5, respectively). The PEG group is capable of modulating the molecule size and the distance between fluorine atom and the stilbene core structure without affecting Aβ plaque-specific binding affinity.

EXAMPLE 55

Film Autoradiography

Brain sections from AD subjects were obtained by freezing the brain in powdered dry ice and cut into 20 micrometer-thick sections. The sections were incubated with [$^{18}$F]tracers (200,000-250,000 cpm/200 μl) for 1 hr at room temperature. The sections were then dipped in saturated Li$_2$CO3 in 40% EtOH (two two-minute washes) and washed with 40% EtOH (one two-minute wash) followed by rinsing with water for 30 sec. After drying, the $^{18}$F-labeled sections were exposed to Kodak MR film overnight.

EXAMPLE 56

In Vivo Plaque Labeling with [$^{18}$F]12b and [$^{18}$F]12d

The in vivo evaluation was performed using either double transgenic APP/PS1 or single transgenic APP2576 mice which were kindly provided by AstraZeneca. After anesthetizing with 1% isoflurane, 250-300 μCi of [$^{18}$F]12b or [$^{18}$F]12d in 200 μl of 0.1% BSA solution was injected through the tail vein. The animals were allowed to recover for 60 min and then killed by decapitation. The brains were immediately removed and frozen in powdered dry ice. Sections of 20 micrometers were cut and exposed to Kodak MR film for overnight. Ex vivo film autoradiograms were thus obtained.

EXAMPLE 57

Organ Distribution in Normal Mice

While under isoflurane anesthesia, 0.15 mL of a 0.1% bovine serum albumin solution containing [$^{18}$F]tracers (5-10 μCi) were injected directly into the tail vein of ICR mice (22-25 g, male) The mice (n=3 for each time point) were sacrificed by cervical dislocation at 120 min post injection. The organs of interest were removed and weighed, and the radioactivity was assayed for radioactivity content with an automatic gamma counter. The percentage dose per organ was calculated by a comparison of the tissue counts to suitably diluted aliquots of the injected material. Total activities of blood were calculated under the assumption that they were 7% of the total body weight. The % dose/g of samples was calculated by comparing the sample counts with the count of the diluted initial dose.

TABLE 2

Biodistribution in ICR mice after iv injection of [$^{18}$F] 12a-d in 0.1% BSA (% dose/g, avg of 3 mice ± SD)

|  | 2 min | 30 min | 1 hr | 2 hr |
|---|---|---|---|---|
| 2A: 12b |  |  |  |  |
| Organ |  |  |  |  |
| Blood | 3.14 ± 0.69 | 2.80 ± 0.44 | 2.51 ± 0.57 | 2.03 ± 0.25 |
| Heart | 6.25 ± 1.79 | 2.18 ± 0.32 | 2.13 ± 0.50 | 1.53 ± 0.08 |
| Muscle | 1.06 ± 0.39 | 1.78 ± 0.34 | 1.45 ± 0.26 | 0.90 ± 0.06 |
| Lung | 6.87 ± 1.36 | 3.20 ± 0.54 | 3.04 ± 0.96 | 2.42 ± 0.36 |
| Kidney | 10.95 ± 2.63 | 6.31 ± 0.58 | 5.68 ± 1.24 | 2.05 ± 1.58 |
| Spleen | 4.57 ± 1.07 | 1.81 ± 0.24 | 1.48 ± 0.91 | 1.54 ± 0.17 |
| Liver | 21.5 ± 4.44 | 13.0 ± 0.72 | 13.2 ± 2.53 | 7.20 ± 0.59 |
| Skin | 1.18 ± 0.23 | 2.36 ± 0.29 | 2.07 ± 0.40 | 1.23 ± 0.16 |
| Brain | 7.77 ± 1.70 | 1.59 ± 0.22 | 1.61 ± 0.39 | 1.39 ± 0.08 |
| Bone | 1.43 ± 0.09 | 1.22 ± 0.17 | 1.77 ± 0.64 | 2.74 ± 0.08 |
| 2B: 12a, 12c, 12d |  |  |  |  |
| 12a |  |  |  |  |
| Blood | 2.64 ± 0.55 | 2.42 ± 0.27 | 2.04 ± 0.16 | 2.77 ± 0.63 |
| Brain | 8.14 ± 2.03 | 3.00 ± 0.16 | 2.60 ± 0.22 | 2.14 ± 0.06 |
| Bone | 1.89 ± 0.25 | 1.40 ± 0.11 | 1.71 ± 0.23 | 2.88 ± 0.07 |
| 12c |  |  |  |  |
| Blood | 3.22 ± 0.20 | 1.88 ± 0.08 | 1.81 ± 0.48 | 1.60 ± 0.12 |
| Brain | 6.59 ± 0.19 | 1.27 ± 0.03 | 1.20 ± 0.10 | 1.21 ± 0.06 |
| Bone | 2.31 ± 0.12 | 1.00 ± 0.02 | 0.98 ± 0.27 | 1.50 ± 0.05 |

TABLE 2-continued

Biodistribution in ICR mice after iv injection of [$^{18}$F] 12a-d in 0.1% BSA (% dose/g, avg of 3 mice ± SD)

|  | 2 min | 30 min | 1 hr | 2 hr |
|---|---|---|---|---|
| 12d |  |  |  |  |
| Blood | 4.99 ± 0.38 | 4.66 ± 0.06 | 2.89 ± 0.11 | 2.59 ± 0.18 |
| Brain | 7.30 ± 1.05 | 2.43 ± 0.03 | 1.77 ± 0.11 | 1.62 ± 0.03 |
| Bone | 2.24 ± 0.21 | 2.29 ± 0.21 | 1.66 ± 0.01 | 2.35 ± 0.27 |

The radioactive compounds, including [$^{18}$F]12a-d, penetrated intact blood-brain barrier showing excellent brain uptake in normal mice (6.6-8.1% dose/g brain) at 2 min post iv injection (Table 2A & B). Since normal mice were used for the biodistribution experiments, no Aβ plaques in the brain is expected in these young mice; therefore, the labeled agents, [$^{18}$F]12a-d, washed out from the brain quickly (1.2-2.6% dose/g brain) at 60 min post iv injection. The high initial uptake and rapid washout in normal mouse brain (with no Aβ plaques in the brain) are highly desirable properties for Aβ plaque-targeting imaging agents. The values reported in Table 2 are comparable to those reported for [$^{11}$C]PIB and [$^{11}$C]SB-13 (Mathis C A, et al., *Curr Pharm Des.* 2004; 10:1469-92; Ono M, et al., *Nucl Med Biol.* 2003; Mathis C A, et al., *J Med. Chem.* 2003).

A detailed biodistribution of [$^{18}$F]12b is shown in Table 2A. It appears that at 2 min after injection the compound was taken up in the liver, kidney, lungs and muscle, reflecting a general blood perfusion pattern. The bone uptake at 120 min was high (2.74% dose/g) suggesting there may be in vivo defluorination. However, the free fluorine are not taken up by brain tissue; therefore, the bone uptake was relatively low. The other PEG stilbene derivatives, 12a,c,d, showed similar biodistribution patterns (Table 2B).

EXAMPLE 58

Partition Coefficient

Partition coefficients were measured by mixing the [$^{18}$F] tracer with 3 g each of 1-octanol and buffer (0.1 M phosphate, pH 7.4) in a test tube. The test tube was vortexed for 3 min at room temperature, followed by centrifugation for 5 min. Two weighed samples (0.5 g each) from the 1-octanol and buffer layers were counted in a well counter. The partition coefficient was determined by calculating the ratio of cpm/g of 1-octanol to that of buffer. Samples from the 1-octanol layer were re-partitioned until consistent partitions of coefficient values were obtained (usually the 3rd or 4th partition). The measurement was done in triplicate and repeated three times.

It will be understood to those of ordinary skill in the art that the same can be performed within a wide and equivalent range of conditions, formulations, and other parameters without affecting the scope of the invention or any embodiment thereof. All patents, patent applications, and publications cited herein are fully incorporated by reference herein in their entirety.

What is claimed is:

1. A compound of Formula I,

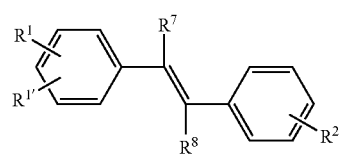

or a pharmaceutically acceptable salt or prodrug thereof, wherein:

$R^1$ is $NR^aR^b$, wherein $R^a$ and $R^b$ are independently hydrogen or $C_{1-4}$ alkyl;

$R^{1'}$ is hydrogen;

$R^2$ is selected from the group consisting of i. hydroxyl, $C_{1-4}$Alkoxy, $(C_1-C_4)$-alkyloxoAlk$(C_1-C_4)$oxy, $(C_1-C_4)$-alkyloxo$(C_1-C_4)$-alkyloxo$(C_1-C_4)$alkoxy, $(C_1-C_4)$-alkyloxo$(C_1-C_4)$-alkyloxo$(C_1-C_4)$-alkyloxo$(C_1-C_4)$alkoxy, carboxy$(C_1-C_4)$Alkyl, halo$(C_1-C_4)$alkoxy, halo$(C_1-C_4)$-alkyloxo $(C_1-C_4)$alkoxy, halo$(C_1-C_4)$alkyloxo$(C_1-C_4)$alkyloxo$(C_1-C_4)$-alkyloxy, halo$(C_1-C_4)$alkyloxo$(C_1-C_4)$alkyloxo$(C_1-C_4)$alkyloxo$(C_1-C_4)$alkyloxy, halo$(C_1-C_4)$alkyl, $NR^6R^{6'}$, phenyl$(C_1-C_4)$alkyl, $^{18}$F$(C_1-C_4)$alkoxy, $^{18}$F$(C_1-C_4)$alkyloxo$(C_1-C_4)$alkoxy, $^{18}$F$(C_1-C_4)$alkyloxo$(C_1-C_4)$alkyloxo$(C_1-C_4)$alkyloxy, $^{18}$F$(C_1-C_4)$alkyloxo$(C_1-C_4)$alkyloxo$(C_1-C_4)$alkyloxo$(C_1-C_4)$alkyloxy, $^{18}$F$(C_1-C_4)$alkyl, wherein $R^6$ and $R^{6'}$ are independently selected from the group consisting of hydrogen, hydroxy$(C_1-C_4)$alkyl and $C_1-C_4$alkyl;

ii.

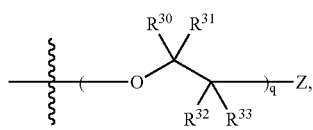

where q is an integer from one to 10; Z is selected from the group consisting of $^{18}$F, $^{18}$F substituted benzoyloxy, $^{18}$F substituted $(C_{1-4})$alkoxy, $^{18}$F substituted benzyloxy, optionally $^{18}$F-phenoxy, $^{18}$F substituted phenyl$(C_{1-4})$alkyl, $^{18}$F substituted aryloxy, and a $^{18}$F substituted $C_{6-10}$ aryl, optionally $^{18}$F-phenyl; and $R^{30}$, $R^{31}$, $R^{32}$ and $R^{33}$ are in each instance independently selected from the group consisting of hydrogen, hydroxy, $C_{1-4}$ alkoxy, $C_{1-4}$ alkyl and hydroxy$(C_{1-4})$alkyl;

iii.

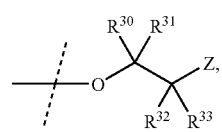

where Z, $R^{30}$, $R^{31}$, $R^{32}$ and $R^{33}$ are as described above;

iv.

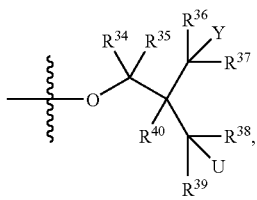

where Y is selected from the group consisting of $^{18}F$, $^{18}F$ substituted benzoyloxy, $^{18}F$ substituted phenyl($C_{1-4}$)alkyl, $^{18}F$ substituted aryloxy optionally $^{18}F$-phenoxy and $^{18}F$ substituted $C_{6-10}$ aryl, optionally $^{18}F$-phenyl;

U is selected from the group consisting of hydrogen, hydroxy, $^{18}F$, $^{18}F$ substituted benzoyloxy, $^{18}F$ substituted phenyl($C_{1-4}$)alkyl, $^{18}F$ substituted aryloxy, optionally $^{18}F$-phenoxy and $^{18}F$ substituted $C_{6-10}$ aryl, optionally $^{18}F$-phenyl; and $R^{34}$, $R^{35}$, $R^{36}$, $R^{37}$, $R^{38}$, $R^{39}$ and $R^{40}$ are in each instance independently selected from the group consisting of hydrogen, hydroxy, $C_{1-4}$ alkoxy, $C_{1-4}$ alkyl, and hydroxy ($C_{1-4}$)alkyl; and $R^7$ and $R^8$ are in each instance independently selected from the group consisting of halogen, hydrogen, hydroxy, amino, methylamino, dimethylamino, $C_{1-4}$ alkoxy, $C_{1-4}$ alkyl, and hydroxy($C_{1-4}$)alkyl, wherein at least one of $R^7$ and $R^8$ is halogen.

2. The compound of claim 1 wherein $R^7$ and $R^8$ are hydrogen or fluorine, wherein at least one of $R^7$ and $R^8$ is fluorine.

3. The compound of claim 1, wherein $R^2$ is ii.

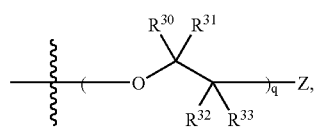

wherein Z, $R^{30}$, $R^{31}$, $R^{32}$ and $R^{33}$ are as described above.

4. The compound of claim 3, wherein q is an integer from 2 to 5.

5. The compound of claim 4, wherein $R^{30}$, $R^{31}$, $R^{32}$ and $R^{33}$ are, in each instance, hydrogen.

6. The compound of claim 5, wherein q is an integer from 3 to 4.

7. The compound of claim 6, wherein Z is $^{18}F$.

8. The compound of claim 7, having the following formula:

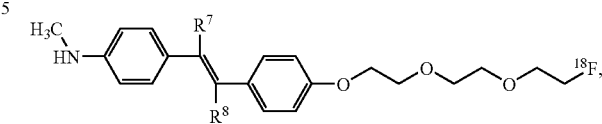

wherein one of $R^7$ and $R^8$ is hydrogen, and the other is halogen.

9. The compound of claim 7, having the following formula:

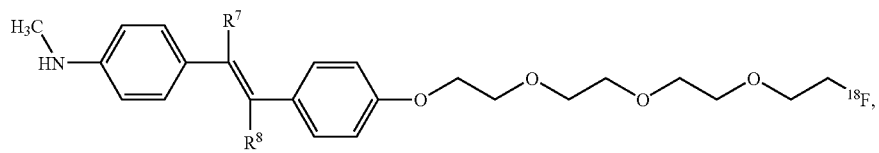

wherein one of $R^7$ and $R^8$ is hydrogen, and the other is halogen.

10. The compound of claim 1, wherein $R^2$ is iii.

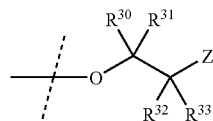

wherein Z, $R^{30}$, $R^{31}$, $R^{32}$ and $R^{33}$ are as described above.

11. The compound of claim 10, wherein Z is $^{18}F$.

12. The compound of claim 11, wherein $R^{30}$, $R^{31}$, $R^{32}$ and $R^{33}$ are, in each instance, hydrogen.

13. The compound of claim 1, wherein $R^2$ is iv.

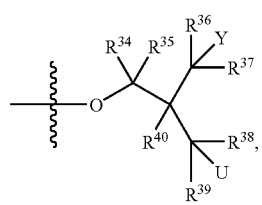

wherein U is hydroxy.

14. The compound of claim 13, wherein $R^{34}$, $R^{35}$, $R^{36}$, $R^{37}$, $R^{38}$, $R^{39}$ and $R^{40}$ are, in each instance, hydrogen.

15. The compound of claim 14, having the following structure:

[Chemical structure: H3C-NH-C6H4-C(R7)=C(R8)-C6H4-O-CH2-CH(CH2-18F)-OH]

wherein one of $R^7$ and $R^8$ is hydrogen, and the other is halogen.

16. A compound of Formula II,

[Chemical structure of Formula II: R1-substituted phenyl-C(R7)=C(R8)-phenyl-R2]

II wherein, $R^1$ is selected from the group consisting of:

a. $NR^aR^b$, wherein $R^a$ and $R^b$ are independently hydrogen, $C_{1-4}$ alkyl, $(CH_2)_dX$, where X is $^{18}F$, and d is an integer between 1 and 4, or $R^a$ and $R^b$ are both oxygen to form a nitro;

b. hydroxy, c. $C_{1-4}$ alkoxy, and d. hydroxy($C_{1-4}$)alkyl;

$R^2$ is selected from the group consisting of:

i.

[Chemical structure with R30, R31, R32, R33, O, Z, q]

wherein q is an integer from 2 to 10; Z is selected from the group consisting of $^{18}F$, $^{18}F$ substituted benzoyloxy, $^{18}F$ substituted ($C_{1-4}$)alkoxy, $^{18}F$ substituted benzyloxy, $^{18}F$ substituted phenyl($C_{1-4}$)alkyl, $^{18}F$ substituted aryloxy, and a $^{18}F$ substituted $C_{6-10}$ aryl; and $R^{30}$, $R^{31}$, $R^{32}$ and $R^{33}$ are in each instance independently selected from the group consisting of hydrogen, hydroxy, $C_{1-4}$ alkoxy, $C_{1-4}$ alkyl and hydroxy($C_{1-4}$)alkyl;

ii.

[Chemical structure with R30, R31, R32, R33, O, Z]

wherein Z, $R^{30}$, $R^{31}$, $R^{32}$ and $R^{33}$ are as described above, and iii.

[Chemical structure with R34, R35, R36, R37, R38, R39, R40, O, Y, U]

wherein Y is selected from the group consisting of $^{18}F$, $^{18}F$ substituted benzoyloxy, $^{18}F$ substituted phenyl($C_{1-4}$)alkyl, $^{18}F$ substituted aryloxy, and $^{18}F$ substituted $C_{6-10}$ aryl;

U is selected from the group consisting of hydrogen, hydroxy, $^{18}F$, $^{18}F$ substituted benzoyloxy, $^{18}F$ substituted phenyl($C_{1-4}$)alkyl, $^{18}F$ substituted aryloxy, and $^{18}F$ substituted $C_{6-10}$ aryl; and $R^{34}$, $R^{35}$, $R^{36}$, $R^{37}$, $R^{38}$, $R^{39}$ and $R^{40}$ are in each instance independently selected from the group consisting of hydrogen, $^{18}F$, hydroxy, $C_{1-4}$ alkoxy, $C_{1-4}$ alkyl, and hydroxy($C_{1-4}$)alkyl;

and $R^7$ and $R^8$ are in each instance independently selected from the group consisting of hydrogen, hydroxy, amino, methylamino, dimethylamino, $C_{1-4}$ alkoxy, $C_{1-4}$ alkyl, and hydroxy($C_{1-4}$)alkyl.

17. The compound of claim 16, wherein $R^1$ is $NR^aR^b$, wherein $R^a$ and $R^b$ are independently hydrogen or $C_{1-4}$ alkyl.

18. The compound of claim 17, wherein $R^2$ is i.

[Chemical structure with R30, R31, R32, R33, O, Z, q]

where Z, $R^{30}$, $R^{31}$, $R^{32}$ and $R^{33}$ are as described above.

19. The compound of claim 18, wherein q is an integer from 2 to 5.

20. The compound of claim 19, wherein $R^7$ and $R^8$ are each hydrogen.

21. The compound of claim 20, wherein $R^{30}$, $R^{31}$, $R^{32}$ and $R^{33}$ are, in each instance, hydrogen.

22. The compound of claim 21, having the following formula:

[Chemical structure: H3C-NH-C6H4-CH=CH-C6H4-O-CH2CH2-O-CH2CH2-O-CH2CH2-18F]

23. The compound of claim 21, having the following formula:

$$H_3C-NH-C_6H_4-CH=CH-C_6H_4-O-CH_2CH_2-O-CH_2CH_2-O-CH_2CH_2-O-CH_2CH_2-{}^{18}F$$

24. The compound of claim 17, wherein $R^2$ is ii.

[structure showing $-O-C(R^{30})(R^{31})-C(R^{32})(R^{33})-Z$]

wherein Z, $R^{30}$, $R^{31}$, $R^{32}$ and $R^{33}$ are as described above.

25. The compound of claim 24, wherein Z is $^{18}F$.

26. The compound of claim 25, wherein $R^7$ and $R^8$ are each hydrogen.

27. The compound of claim 26, wherein $R^{30}$, $R^{31}$, $R^{32}$ and $R^{33}$ are, in each instance, hydrogen.

28. The compound of claim 17, wherein $R^2$ is iii.

[branched structure with $R^{34}$, $R^{35}$, $R^{36}$, $R^{37}$, $R^{38}$, $R^{39}$, $R^{40}$, Y, U]

wherein U is hydroxy.

29. The compound of claim 28, wherein $R^{34}$, $R^{35}$, $R^{36}$, $R^{37}$, $R^{38}$, $R^{39}$ and $R^{40}$ are, in each instance, hydrogen.

30. The compound of claim 29, having the following structure:

[Structure: H3C-NH-phenyl-CH=CH-phenyl-O-CH2-CH(CH2-18F)-CH2-OH]

31. A compound of Formula III:

$$R^{41}-(CH_2)_n-C_6H_4-C(R^7)=C(R^8)-C_6H_4-{}^{18}F$$  III wherein, n is an integer between 1 and 4;

$R^7$ and $R^8$ are in each instance independently selected from the group consisting of hydrogen, hydroxy, amino, methylamino, dimethylamino, $C_{1-4}$ alkoxy, $C_{1-4}$ alkyl, and hydroxy($C_{1-4}$)alkyl; and $R^{41}$ is selected from the group consisting of hydroxy and $NR^aR^b$, wherein $R^a$ and $R^b$ are independently hydrogen, $C_{1-4}$ alkyl, or $R^a$ and $R^b$ are both oxygen to form a nitro.

32. The compound of claim 31, wherein n is one, and $R^{41}$ is selected from the group consisting of hydroxy, methylamino and dimethylamino.

33. A pharmaceutical composition comprising a compound of claim 1, 16 or 31.

34. A diagnostic composition for imaging amyloid deposits, comprising a radiolabeled compound of claim 1, 16 or 31.

35. A method of imaging amyloid deposits, comprising:
a. introducing into a mammal a detectable quantity of a diagnostic composition of claim 34;
b. allowing sufficient time for the labeled compound to be associated with amyloid deposits; and
c. detecting the labeled compound associated with one or more amyloid deposits.

* * * * *